United States Patent [19]
Yoshikawa et al.

[11] Patent Number: 6,082,175
[45] Date of Patent: Jul. 4, 2000

[54] ELECTRONIC COMPONENT HAVING TERMINAL CONNECTING LEADS WITH A HIGH TEMPERATURE CERAMIC ELEMENT AND A METHOD OF MAKING THE SAME

[75] Inventors: Takaya Yoshikawa; Katsuhisa Yabuta; Masaya Ito; Hisaharu Nishino, all of Nagoya, Japan

[73] Assignee: NGK Spark Plug Co., Ltd., Nagoya, Japan

[21] Appl. No.: 08/950,136

[22] Filed: Oct. 14, 1997

[30] Foreign Application Priority Data

Oct. 14, 1996 [JP] Japan .................................. 8-270625
Oct. 9, 1997 [JP] Japan .................................. 9-293322

[51] Int. Cl.$^7$ .................................................. G01N 27/12
[52] U.S. Cl. ........................ 73/23.31; 73/31.05; 204/426
[58] Field of Search ............................ 73/31.05, 23.31; 204/426

[56] References Cited

U.S. PATENT DOCUMENTS

| | | | |
|---|---|---|---|
| 4,596,132 | 6/1986 | Takami et al. ................. | 73/31.05 X |
| 4,983,271 | 1/1991 | Kato et al. .................... | 204/426 |
| 5,246,562 | 9/1993 | Weyl et al. .................... | 204/424 |
| 5,329,806 | 7/1994 | McClanahan et al. .......... | 73/31.05 |
| 5,467,636 | 11/1995 | Thompson et al. ............. | 73/23.31 |
| 5,739,414 | 4/1998 | Paulus et al. .................. | 73/31.05 X |
| 5,817,920 | 10/1998 | Kuisell et al. .................. | 73/23.31 |

FOREIGN PATENT DOCUMENTS 41 26 378 A1 4/1992 Germany .
637326 9/1994 Japan .

*Primary Examiner*—Daniel S. Larkin
*Attorney, Agent, or Firm*—Morgan, Lewis & Bockius LLP

[57] ABSTRACT

This discloses an electronic component of a miniature size to be used as e.g. automobile engine peripheral components, such as an exhaust gas oxygen sensor, a heat sensor, and a heater. More specifically, the invention provides an electronic component integral with a heat resistant terminal that is pressure-fitting or shrink-fitted on a ceramic element of the electronic component. This electronic components shows great mechanical and electrical performance, withstanding the high temperature environment over 400 and up to 800° C. to which the ceramic element of the component required expose.

The terminal incorporated in this high temperature electronic component comprises a plurality of metal wire leads that electrically connect to a surface of a bar-like ceramic element, at least two ceramic insulators that surround the leads, and a thermal resistant metal ring that shrink-fits or pressure-fits around the ceramic insulators so that the metal leads press in a radial direction holding the element firmly.

The thermal resistant metal ring to be used for this shrink fit or pressure fit is preferably made of an alloy, such as Incoloy 909, Inconel 650, and Waspaloy, and the like, thereby preventing the metal leads from coming off at high temperature.

The terminal integrated with the ceramic element by the shrink fitting method according to the invention, minimizes the number of parts, attaining a miniaturization of such high temperature electronic component at a low cost.

23 Claims, 14 Drawing Sheets

ELECTRONIC COMPONENT HAVING TERMINAL CONNECTING LEADS WITH A HIGH TEMPERATURE CERAMIC ELEMENT AND A METHOD OF MAKING THE SAME

BACKGROUND OF THE INVENTION

1. Field of the Invention

The present invention generally relates to electronic devices to be placed in a high temperature environment, such as an automobile engine compartment, particularly it relates to a terminal unitarily assembled with a ceramic element of the electronic components, such as an oxygen sensor, a NOx sensor, a CO sensor, a $CO_2$ sensor, a heat sensor, a ceramic heater, and a ceramic glow plug placed in a high temperature gas environment, for instance, an exhausted gas from automobile vehicle engines.

Specifically, this invention relates to a electronic component of a miniature size having a ceramic element unitarily connected to metal wire leads, the electronic component assembly withstanding the gas environment from an ambient temperature up to a high temperature of 800° C.

This invention further relates to a method of assembling parts, such as a ceramic element and leads, into a unitary electronic component to be used at the high temperature, minimizing the number of the parts.

2. Description of the Related Art

Many high-temperature components are required in a high temperature periphery of vibrant automobile engines. These components include oxygen sensors, NOx sensors, and heat sensors that are placed in exhaust pipes of internal combustion engines.

These electrical control components output electrical signals to a computer control circuit through resin-covered metal wires. These resin covered metal wires do not withstand the high temperature of more than 300° C.

In order to connect these low temperature resistant wires with a ceramic element of the electrical component for high temperature use, conventionally a terminal assembly as shown in FIG. 21 referring as a Related Art of the Invention has been recommended.

Referring to this terminal assembly of the Related Art, a high temperature ceramic element 150 is electrically and mechanically connected to sheathed lead wires 152 via metal leads 153. Electrodes 151 formed on the ceramic element 150 are contacted with the metal leads 153. Two ceramic plates 154 having notches insulate the metal leads 153 from a metal fastener 157 by covering the metal leads 153. Two half pipes 155 having a U shape in cross section hold the ceramic plate 154 therein.

A spring plate 156 having a triangle shape in cross section is attached on an outer side of the each half pipe. The tubular metal casing 157 presses in the metal leads 153, the ceramic plates 154, the half pipes and the spring plates 156 in a radial direction, aligning them and forming a terminal assembly unit. In this terminal assembly unit, the metal lead 153 has a J shape portion which bends like a spring and sit in the notch of the ceramic plate 154 to hold the element when the ceramic element slides into the unit and the spring plates 156 also press the ceramic plates in. These metal leads 153 form a female connecting portion which receives the electrodes 151 of the ceramic elements 150 and clamps the ceramic elements 150 with a strong fastening pressure given from the spring plates 156.

THE SUMMARY OF THE INVENTION

Although the above terminal assembly unit of the Related Art can be used as a terminal for the electronic component or device to be used in a high temperature and vibrant environment as in an automobile engine compartment, it does not satisfy a future requirement for the electronic component; i.e., every electronic component will be smaller, more strenuous and less expensive, performing better than before in a severe environment.

One of the drawbacks in the above terminal assembly unit is that it is very difficult to make the unit compact in size, because the spring is considered necessary to hold the metal leads on. If this structure of the terminal assembly is used in miniaturization of the electronic component, the fastening strength of the spring in the high temperature and vibrant environment will be critical, because a heat source becomes closer to the terminal due to such miniaturization.

The engine peripheral components such as Oxygen sensors, NOx sensors, heat sensors, and glow plugs are often exposed to the gas with a temperature of about 400–1000° C. and even in a vibrant condition. Therefore, the terminal structure and materials for these high temperature components are very important in miniaturization because not only thermal (heat) resistance but oxidation resistance must be considered.

The conventional terminal structure as described in the Related Art will not withstand a temperature of more than 400° C. because the metal spring in the terminal usually starts losing its elasticity beyond such a temperature.

If the terminal is loosened, the oxidation of the metal leads accelerates due to air intrusion into the terminal, and an electrical contact resistance between the metal lead and the electrode portion increases causing an electrical malfunction in an electrical control unit that receives or outputs electrical signals from or to the electronic component element.

Another drawback of the terminal of the Related Art is that the terminal assembly is composed of many parts resulting in complicated technology required for assembly.

It is therefore an object of the present invention to provide an electronic component integral with its terminal in compact size and with its heat resistance and oxidation resistance at high temperature of more than 400° C.

It is another object of the present invention to provide a terminal structure unitary with an electronic component (or device) that has a high temperature resistance and a vibrant resistance and can be used as an automobile engine peripheral component.

It is still another object of the present invention to provide an electronic component having a miniature terminal that can withstand such a high temperature as 400–800° C.

It is a further object of the present invention to provide a method of making an electronic component including a compact terminal which shows heat resistance at a high temperature.

Briefly, these and other objects of this invention as hereinafter will become more readily apparent as having been attained broadly by an electronic component having a simple and compact terminal structure, i.e., eliminating the spring holding the element of the electronic component as in the Related Art.

The electronic component according to the invention, is assembled unitary or integral with its terminal, i.e. the terminal is fixed to the ceramic element by pressure fit or shrink fit. In other words, once electronic component is united with the terminal leads by the pressure fit or shrink fit at a factory, the terminal leads are not necessarily replaced with other indexable terminal as in the case of the conventional electronic component which is separately made from the terminal.

By utilizing the pressure fit and/or shrink fit in making the electronic component unitary with the terminal, the present invention is attained. In order to accomplish this invention, many factors have to be carefully arranged. One of the factors is a selection of material of the ring used for the shrink fit and/or pressure fit, and the other is a dimensional factor as described in later paragraphs.

According to the invention, there is provided an electronic component to be used as e.g. automobile engine peripheral components, such as an oxygen sensor, a heat sensor, and a heater is provided. More specifically, an electronic component having a compact and thermal resistant terminal is provided. The electronic components according to the invention shows a good mechanical and electrical performance withstanding the high temperature environment beyond 400 up to 800° C. to which the ceramic element of the electronic component is exposed.

The terminal incorporated into this high temperature electronic component according to the invention, comprises a plurality of metallic wire leads that electrically connect to a surface of a bar-like ceramic element, at least two ceramic insulators that surround or cover the leads, and a thermal resistant ring that shrink-fits or pressure-fits around the ceramic insulators so that the metallic leads are pressed in a radial direction holding the element firmly at electrode portions formed on the surface of the element.

In order to attain an electronic product for the purpose of the invention, the thermal (heat) resistant ring for binding the leads against the ceramic elements is used, because the ring is elevated in temperature up to 800° C. The material for this thermal resistance ring usable for the shrink fit or pressure fit is preferably made of an alloy such as Incoloy 909, Inconel 650, and Waspaloy. The alloy having the following range of composition gives a satisfactory result in the shrink fit and/or pressure fit.

The alloy containing at least two elements selected from Fe, Ni, Co, and Cr is preferably used; e.g., an alloy including 1–40 weight percent of Fe and the balance substantially made of Ni, or an alloy including 1–30 weight percent of Co and the balance substantially made of Ni, an alloy including 15–45 percent of Cr and the balance substantially made of Ni, or an alloy including 1–21 percent of Fe and the balance substantially made of Co, or an alloy including 10–20 weight percent of Ni and the balance substantially of Co, or an alloy including 20–31 weight percent of Cr and the balance substantially made of Co, or an alloy including 2–43 weight percent of Ni and the balance substantially made of Fe, or an alloy including 3–23 weight percent of Co and the balance substantially of Fe, or an alloy including 0.5–32 weight percent of Cr and the balance substantially made of Fe.

These alloys prevent a terminal or rather connection unit comprised of the metal leads, the ceramic insulators and the ring, from coming off from the element of the electronic components at such high temperature.

Alternative materials for the resistant ring are a silicon nitride ceramic including a sialon ceramic, silicon whisker reinforced alumina ceramic, or partially stabilized zirconia (PSZ) ceramic because these materials are mechanically strong and withstand high temperatures.

The terminal structure according to the invention becomes very compact in size with the least number of the terminal parts, and a miniaturization of tho high temperature electronic component is realized.

More in detail, the electronic component according to the invention includes the ceramic element of a bar-like shape having an electrode portion formed on the element surface close to one end of the bar element. Another end of the bar-shaped element may be placed e.g. in a high temperature exhaust gas from an internal combustion engine. A preferable material of the ceramic element is a high strength material such as zirconia in the case of sensors detecting oxygen, NOx, temperature, or alumina, or silicon nitride in the case of ceramic heaters or glow plugs.

The ceramic element is exposed to a gaseous atmosphere having a temperature of more than 400° C. up to 800° C. or more. The electrode portion formed on the ceramic element is a heat resistant metal coated on the element surface, including platinum, iridium, palladium rhodium, tungsten, gold, and/or an alloy containing one of these metals.

The electronic component according to the invention includes the metal leads (i.e., conductive wire members) that electrically connect to the electrode portions of the ceramic elements at one end of the metal leads by surrounding and contacting the element. The metal leads run in parallel in a axial direction of the bar-like ceramic element and connect their other ends to the ends of outer resin sheathed wires that send electrical signals from the ceramic element to a control circuit. The metal leads are preferably made of a heat resistant material, such as nickel or the same material as the ring.

The electronic component according to the invention includes a plurality of ceramic bulk insulators which cover the metal leads. The ceramic insulator is made preferably of alumina or silicon nitride because of high mechanical strength that tolerates the pressure or shrink fit. In the case that the ceramic element having a plate-like bar having flat surfaces is used, the shape of the insulator is preferably a plate. In the case that the surface of the ceramic element is round or cylindrical, the insulator surface that contacts the metal leads is formed accordingly in parallel with such round or cylindrical surface of the element. Important is a parallel gap formed by the metal leads sandwiched between the surface of the element and the surface of the ceramic insulator before the shrink fit or the pressure fit process. The number of the insulators is preferably two, because they tend to hold the element and the metal leads firmly in and the pressure-fit or shrink fit assembling process is easy and stable.

The electronic components according to the invention include a thermal resistance ring that fastens the ceramic insulators, the metal leads and the ceramic element into a unitary assembly. The electronic component unitary assembled with the terminal is characterized by the thermal resistant ring which shrink-fits or pressure-fits against the ceramic insulators covering the metal leads that contact the electrode portions formed on a peripheral surface of the ceramic element of the electronic component.

Dimensional factors for the shrink fit or pressure fit is also considered as described later in the Detailed Embodiment Of the Invention.

An overall size of the high temperature electronic component integral with the terminal according to the invention can be made as compact as one to two thirds of that of a conventional high temperature electronic component.

BRIEF DESCRIPTION OF THE DRAWINGS

FIG. 13 A is a view of the ends of two half cylindrical ceramic insulators placed on the metal leads that contact electrode portion formed on cylindrical ceramic element, measuring a dimension across the outer surfaces of the ceramic insulators as shown by reference letter a.

FIG. 13 B is a view of a plan view of a thermal resistant ring that shrink fits or pressure fits onto the ceramic insulators shown in FIG. 13A, measuring an outer diameter and an inner diameter of the ring as shown by reference letters b and d respectively.

PREFERRED EMBODIMENTS OF THE INVENTION

Figure 1:
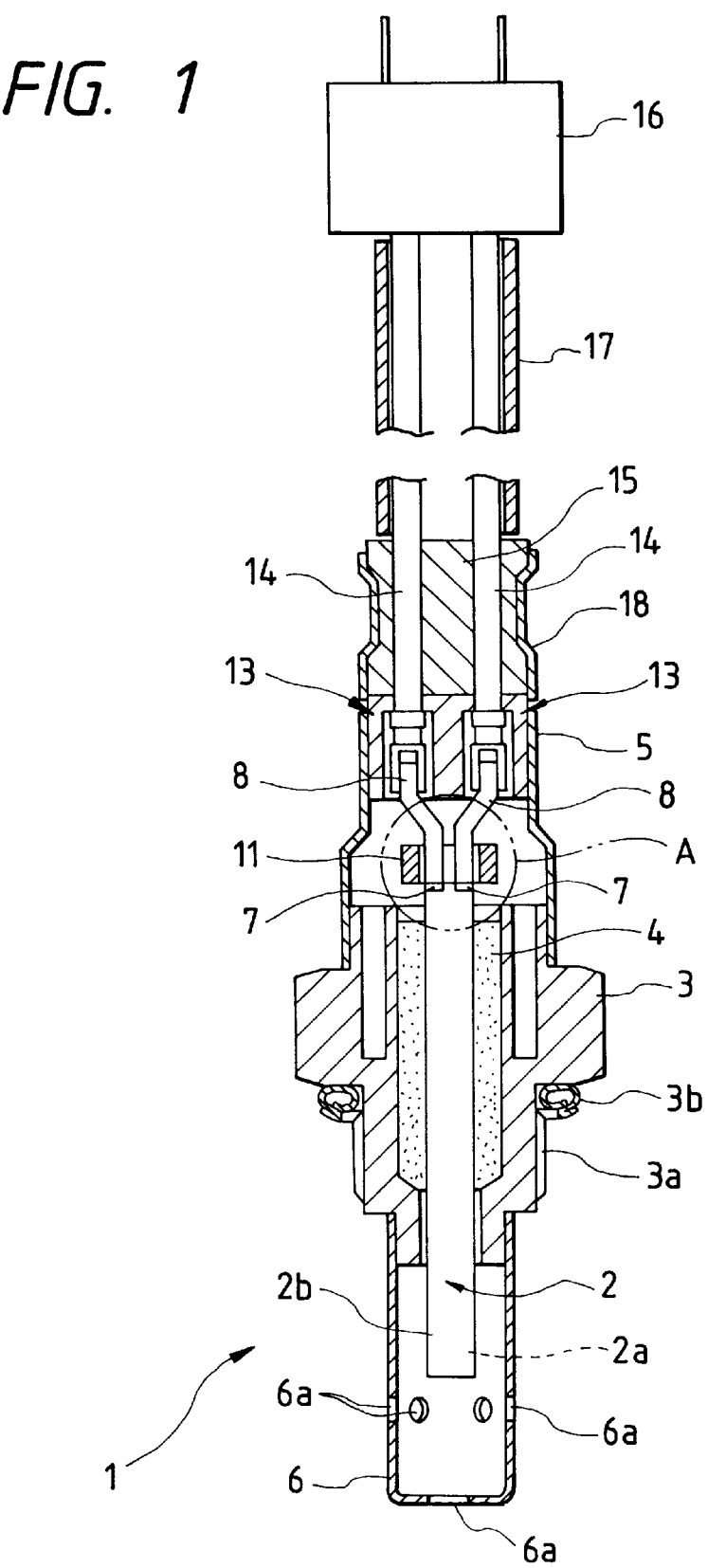
FIG. 1 is a sectional view of an electronic component unitarily assembled with a terminal, embodied e.g. on an oxygen sensor, according to the invention.

FIG.1 shows an embodiment of an electronic component 1 used in a high temperature according to the invention, embodied as an oxygen sensor which detects an oxygen concentration in a exhaust gas emitted from an internal combustion engine.

This electronic component 1 includes a bar-like ceramic element 2 with its one end extending to expose in a hot exhaust gas flowing in an exhaust pipe of the engine. The ceramic element 2 is fixed in a cylindrical metal shell 3 by a glass seal or cement 4. A material of the ceramic element 2 is an electrochemical ceramic, such as a partially stabilized zirconia (PSZ). The metal shell 3 is supported at its one end of the opening formed in the shell 3 with an cylindrical metal casing 5.

Electrode portions 7,7 are formed at one end of the ceramic element 2 and one end of bare metal leads 8,8 contact surfaces of the electrode portions 7,7. The other ends of the metal leads 8,8 are connected to outer leads 14,14 sheathed by resin, as referred as connecting portions 13,13. The electrode portions 7,7 and the metal leads 8,8 and these connecting portions 13,13 are arranged in the metal casing 5. The resin sheath 17, coating the outer leads 14,14, runs through a grommet 15 and connects their other ends to a plug connector 16 which may be further connected with an electronic control unit by a electric harness, etc. An outer protecting tube 18 is extended from the other opening of the metal casing 5 in the axial direction incorporating the grommet 15 in and protects the connecting portions 13,13 from moving.

The metal leads 8,8 contacting the electrode portion 7,7 are unitarily fixed to the end portion of the ceramic element 2 by a ring 11 with a pressure fit or shrink fit of the ring 11 which is shown in the encircled area referenced as A and is described more in detail in later paragraphs referring to FIG. 2 and FIG. 3.

The other end of the bar-like ceramic element 2 is projected from the other opening of the metal shell 3, forming an oxygen-sensing portion 2b for the high temperature gas and a heating portion 2a that heats the sensing portion 2b. The sensing portion 2b is protected by a metal protector 6 which has holes 6a formed thereat through which the high temperature gas communicates.

A threaded portion 3a is provided on the metal shell 3 and a ring gasket 3b is provide with the threaded portion so that electronic component 1 is screwed airtight to an exhaust pipe.

Since the electronic component according to the invention as described above utilizes a ring that pressure fit or shrink fit the metal leads on the ceramic element, an overall size of the components can be made compact.

Figure 2:
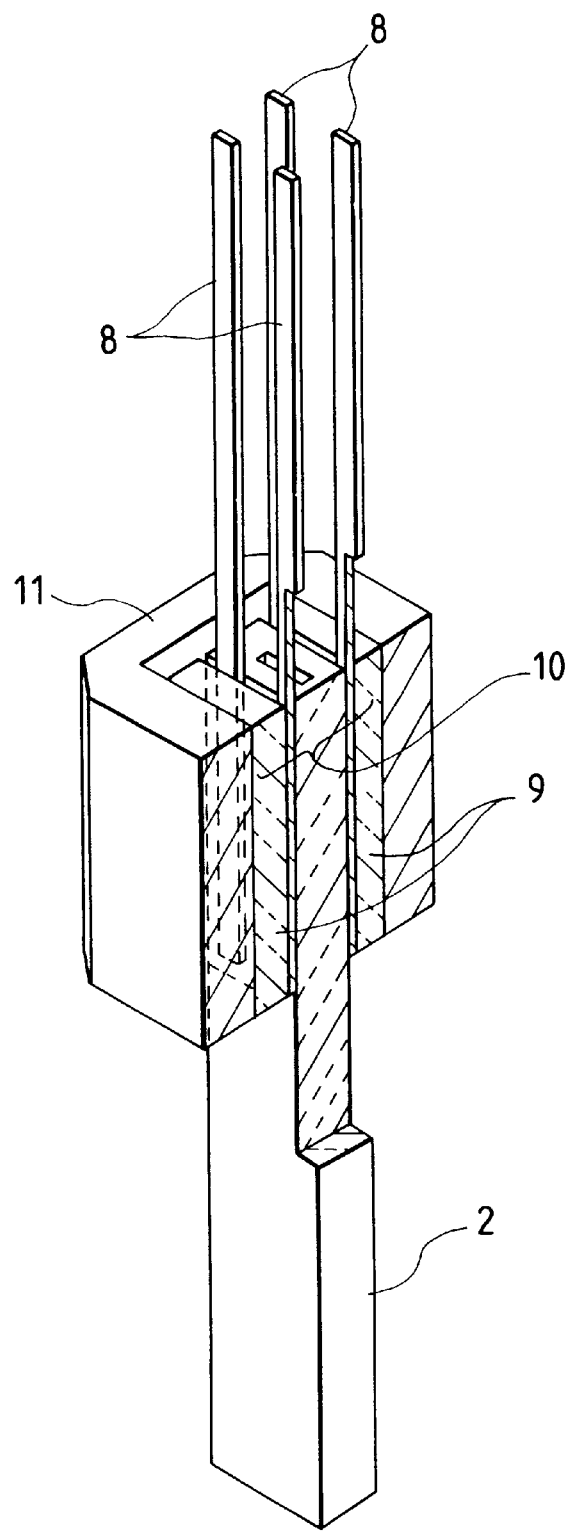
FIG. 2 is a perspective and partial sectional enlarged view of the terminal unitarily assembled to a ceramic element of the electronic component, as indicated by an encircled area (A) in the drawing of FIG. 1.
Figure 3:
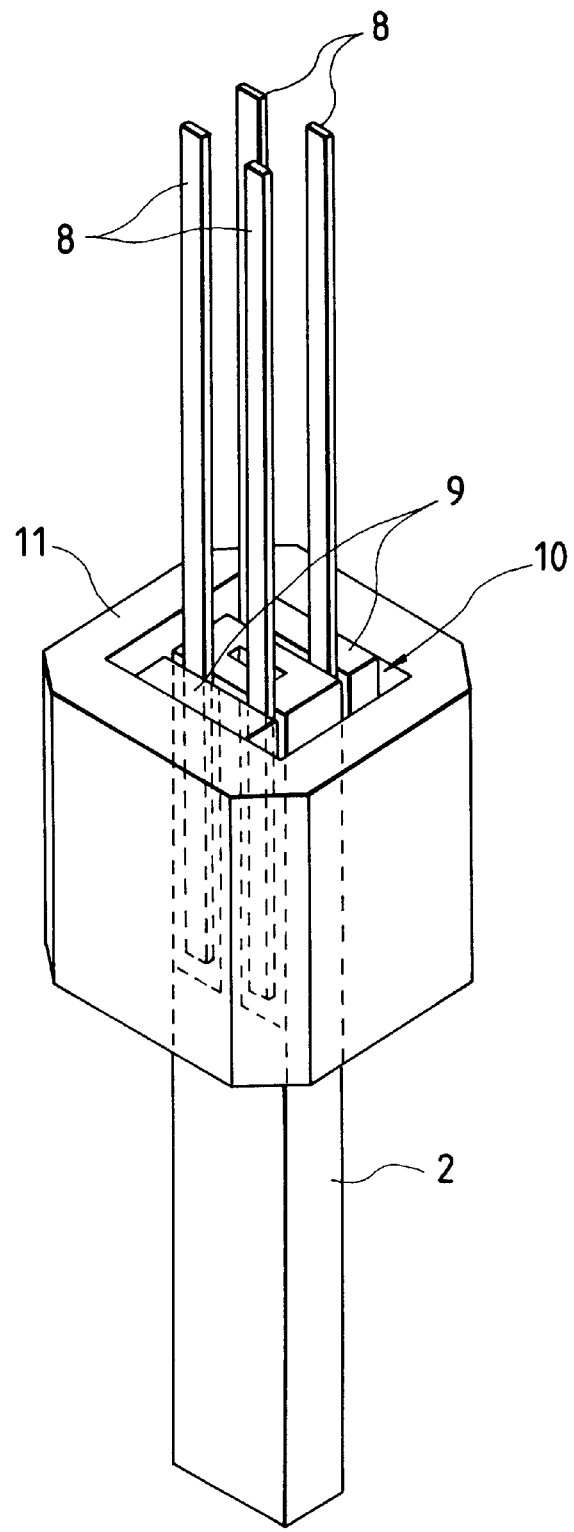
FIG. 3 is a perspective enlarged view of the terminal unitarily assembled to a ceramic element of the electronic component as indicated by the drawing of FIG. 1., showing a unitary structure that a thermal resistant ring, ceramic insulators and metal leads, and the ceramic element are assembled by shrink or pressure fit, forming a terminal of an electronic component.
Figure 4:
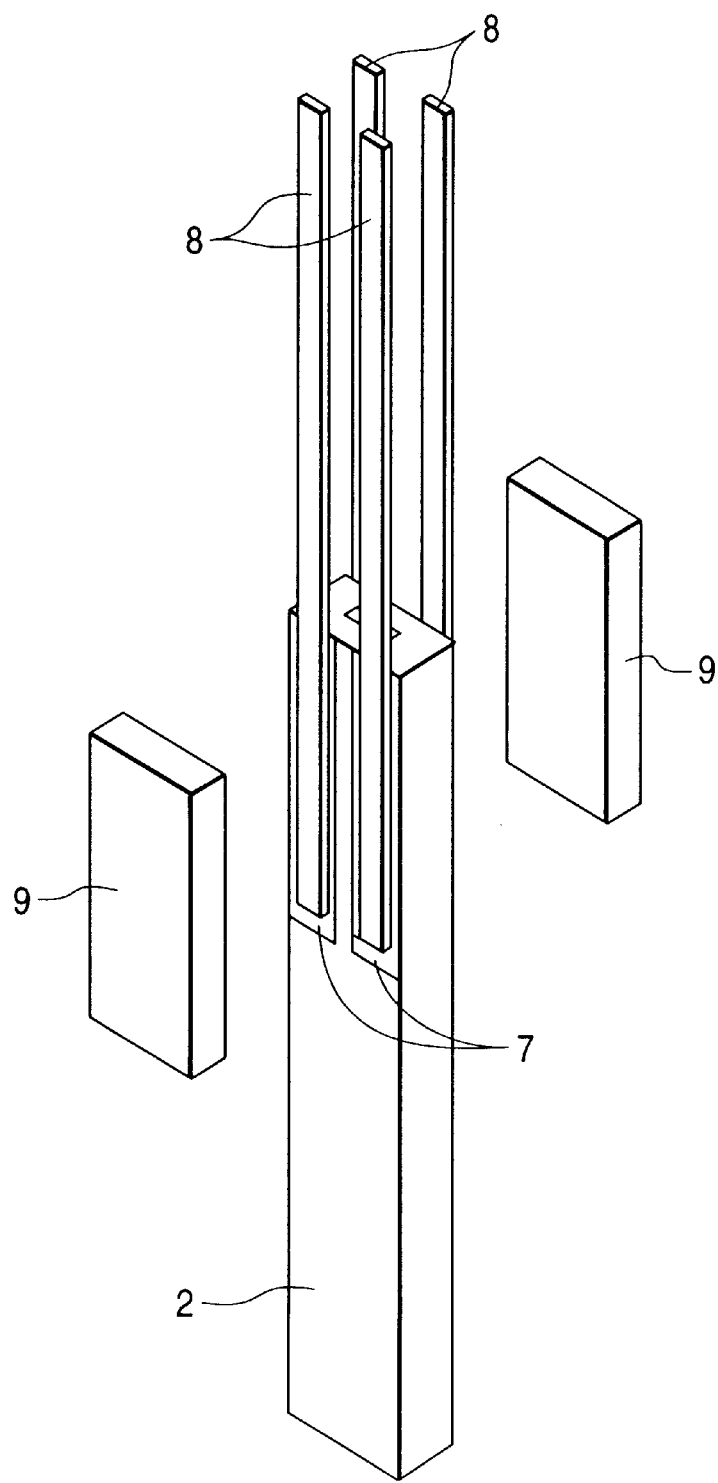
FIG. 4 is a perspective view of a decomposed terminal structure showing a bar-like ceramic element, electrode portions, metal leads, band ceramic insulators, except a thermal resistant ring.

Now referring to FIGS. 2 to 4, a structure of the terminal portion integral with the ceramic element of the electronic components according to the invention is described. A columnar ceramic element 2 has a rectangular shape in cross section. Totally, four electrodes 7,7, are made by coating, e.g. Pt on the surfaces of the ceramic elements as shown in FIG. 4. Two of the electrodes 7 for electrical connection to an oxygen sensing portion are formed by metalization on the one surface close to the end of the ceramic 2 and another two of the electrodes 7 for an electrical connection to a heating portion are formed by metalization on the reverse surface of the ceramic element 2.

A metal lead is placed on each of the electrodes 7,7, a ceramic plate 9 is placed on the two metal leads 8,8 and another ceramic plate 9 is placed on the other two metal leads 8,8, forming a terminal having the four metal leads projecting in parallel along the axis of element2. Then a metal ring 11 having a rectangular cylindrical shape clamps the ceramic plates 9,9 by shrink fitting.

A shrink-fitting force functions in a radial direction of the metal ring 11 pressing the ceramic plates 9 in so that the respective metal leads 8,8 firmly contact the electrode 7,7 of the ceramic element 2. A material for the ring 11 in preferably composed of a thermal resistant alloy having a heat resistant hardness, such as a heat resistant stainless, Inconel (trade name alloy available from International Nickel Co.), Incoloy(trade name alloy available from International Nickel Co.), and Waspaloy(trade name alloy available from United Technology Inc.). The preferable material of the metal ring selected to be used for the shrink fit and/or for the pressure fit is Incoloy 909, Incoloy 650, or Waspaloy, or alloy similar to these trade name alloys. The preferable composition in the alloy contains at least two elements selected from Fe, Ni, Co, and Cr, and the compositional ranges of the alloy are described previously in the Summary of the Invention.

Instead of these heat resistant alloys, other heat resistant materials can be used, e.g. heat resistant ceramic having a strength in the high temperature, such as alumina, Sic whisker reinforced alumina, and silicon nitride including sialon. If the ceramic insulating ring is used as the ring 11 for the shrink-fit or pressure fit, the ceramic plate 9 inserted between the metal leads 8 and the ring 11 is unnecessary, because such a ceramic insulating ring acts as a ceramic plate for insulation and as a binding means to bind the metal leads 8 against the ceramic element 2.

Figure 5:
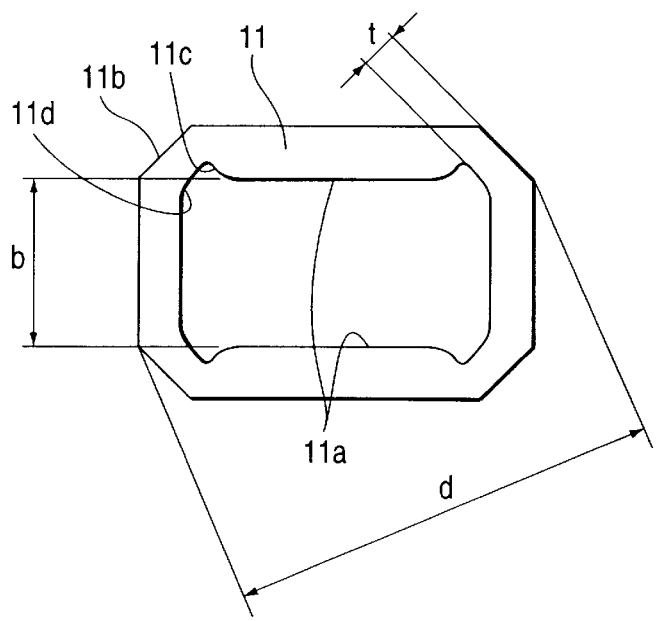
FIG. 5 is a plan view of the thermal resistant ring for shrink or pressure fit, designed according to the invention.

As shown in FIG. 5, one preferable shape of the thermal resistant ring 11 is formed rectangular, having four inner corners 11c concavely cut or arc-cut to lessen a stress concentration of the ring caused by the shrink-fit or pressure fit. The outer four corners are chamfered in about 45 degree angles slanting to the side.

The shrink fit here includes a process in which the thermal resistant ring is firstly heated to the predetermined high temperature which is above the expected temperature of the electronic component in actual use, thereby expanding the shape of the ring outwardly according to a heat expansion ratio of the ring, and then the heated ring is put on the ceramic plates covering the metal leads that surround the ceramic element at the electrode portions of the element. The heated ring can be put on the ceramic with slight pressure. Then the heated rings gradually start shrinking thereby holding or rather clamping the ceramic plates pressing the metal leads in against the ceramic element in a radial inward direction of the ring. This process may be called a hot shrink fit.

The shrink fit here includes a process in which the ceramic plates, the leads, and the ceramic element are cooled in a very low temperature so that these parts shrink, and thereby the shrunken parts are easily inserted in the ring. This process may be called a cool shrink fit.

The pressure fit here includes a process in which the ring is put on the ceramic plates covering the metal leads that surround the ceramic element by pressure, squeezing the ceramic inwardly, pressing the leads against the ceramic element in a radial direction of the ring.

Referring to FIG. 5, the thinnest thickness (t) of the ring measured in a radial direction of the ring is preferably in the range of 2.3 percent to 35 percent of the maximum outer dimension or rather diagonal dimension of the ring. That is, a first dimensional factor expressed by the expression of a>b and $0.023 \leq t \leq 0.35$ is employed regarding the ring design. (The reference letter a is shown in FIG. 6.)

Figure 6:
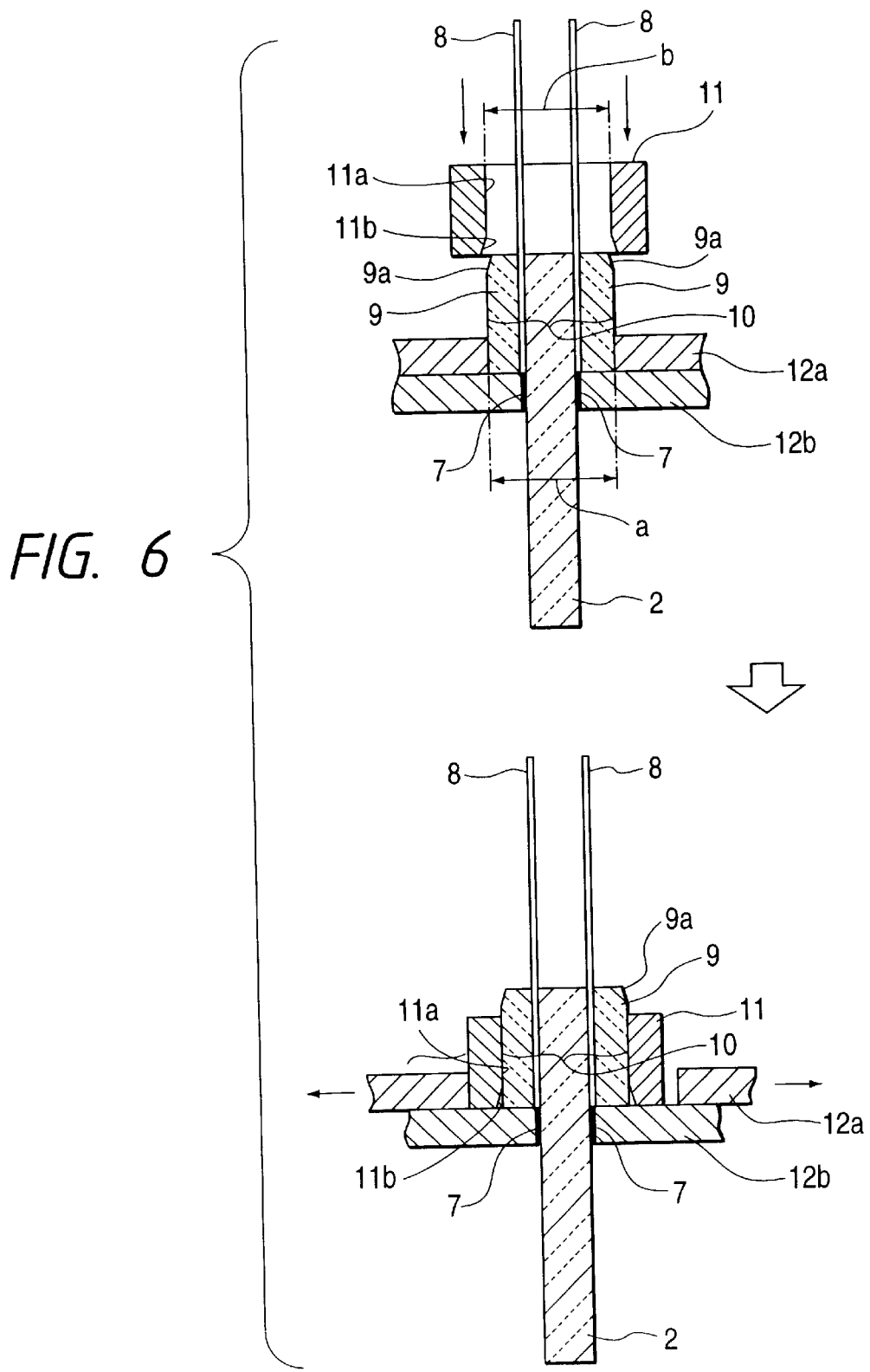
FIG. 6 shows a schematic view of the pressure or shrink fitting process to form a terminal on the ceramic element, showing a pre-assembled stage and a post-assembled stage, according to the invention.

Another dimensional factor in consideration to accomplish the present invention is a post-decomposition interference ($\delta 1$), that is defined by the difference between a post-connection dimensional (a1) and a post-holding dimension (b1), wherein, a1 is the distance measured in a radial direction of the ring, after the shrink fitted ring 11 on the ceramic plates is removed, between the maximum outer surfaces of the ceramic plates opposing each other, as indicated by letter (a) in FIG. 6, and b1 is the distance measured in the same radial direction of the ring, after the shrink fitted ring 11 on the ceramic plates is removed, between the minimum inner surfaces formed in of the metal ring, as indicated by letter (b) in FIG. 5.

The best result of shrink-fit and/or pressure fit is obtained when this post-decomposition interference ($\delta 1$) ranges from 0.23 to 9.3 percent of the post-holding dimension (b1). A secondary dimensional factor expressed by the expression of $0.0023 b1 \leq \delta 1 \leq 0.093 b1$ is referred as a check indicator for the shrink or pressure fit in assemblage.

Still another dimensional factor in consideration to accomplish the invention, is a maximum-temperature fitting interference ($\delta m$) which is defined by the difference between an outer dimension (am) and a holding dimension (bm), wherein, am is the expanded distance measured in a radial direction of the ring between the outer surfaces of the ceramic plates opposing each other in a temperature elevated state of the maximum temperature estimated in actual use without the metal ring on, as indicated by letter (a) in FIG. 6., and wherein, bm is the expanded distance measured in the same radial direction of the ring between the minimum inner surfaces formed in the ring in a temperature elevated state of the maximum temperature estimated in actual use without the ceramic plates inserted in the ring, as indicated by letter (b) in FIG. 5

This maximum-temperature fitting interference ($\delta m$) should not be smaller than 0.1 percent of the holding dimension (bm), otherwise the shrink fitted ring would come off from the ceramic element, resulting in decomposing the terminal leads integral with the electronic component in a vibrant high temperature environment.

Referring to the top drawing of FIG. 6, a pressure fitting process in which the metal ring 11 is ready to put on the ceramic plates 9,9 surrounding the metal loads 8,8 placed on the electrode portion 7,7 formed on the surface of the ceramic elements near the end of ceramic element.

An inner surface 11a partly tapered at an angle of 5 to 30 degrees spreading out forming a slanted opening end 11b is formed at the vicinity of the opening end of a thermal resistant metal ring 11, and a slanting outer surface 9a corresponding to the tapered inner surface 11d of the ring 11 is formed at the end or the ceramic plates 9,9.

A connection unit 10 composed of the bar-like ceramic element 2 including the electrode portions 7,7, bare conductive wires (metal leads) 8,8, and a pair of insulation plates (ceramic plates) 9,9 are held together, the ceramic element 2 being held in the hole made in a bottom jig plate 12b, and pressed in a direction perpendicular to the axis of ceramic element 2 by two top jig plates 12a, forming a temporary fastened state of the connection unit 10.

Then the ring 11 is pressed down onto the connection unit 10 with the slanted opening end 11b of the ring fitting over the slanting outer surfaces 11a of the ceramic plates 9 of the connection unit 10, thereby forming the ring pressure fitted on the connection unit 10.

Similar to the above pressure fitting process, a shrink fit process is done, except the thermal resistant ring 11 and a connection unit 10 undergo different temperature in the shrink fitting process, i.e. for instance, the thermal resistant ring 11 is elevated to a higher temperature before the shrink fitting and then put on the connection unit 10 which is lower in temperature than the ring 11, forming a shrink fitted ring on the ceramic plates 9,9 of the connection unit 10 after the heated ring is cooled.

First Experimental Example

Performance tests, to which an electrode connection structure (hereinafter called an "example") of the ceramic element 2 of the oxygen sensor 1 according to the present invention and the electrode structure (hereinafter called as a "Comparative example") described in the conventional art were subjected at high temperatures to evaluate the endurance will now be described. Note that Incoloy Alloy 909 is heat-resisting steel having Fe, Ni, and Cr added thereto, while Inconel Alloy 750 is a heat-resisting alloy mainly composed of Ni and having Fe and Cr added thereto.

The following samples are used in the foregoing performance tests.

EXAMPLE

The ceramic element 2 is made of partially-stabilized zirconia (hereinafter called as "PSZ") and having a width of 4 mm and a thickness of 1.3 mm. The lead wire 8 is made of Inconel Alloy 750 and having a width of 1.5 mm and a thickness of 0.2 mm.

The insulating plate 9 is formed into a rectangular plate-like shape, made of alumina and having a width of 4 mm and a thickness adjusted such that the clamping interference δ is adjusted as shown in Table 1. Moreover, the post-decomposition interference (δ1) satisfies the range from 0.23% to 9.3% of the post-decomposition holding dimension (b1).

The metal ring 11 is made of Inconel Alloy 909, having a minimum thickness (t) of 0.7 mm, a maximum outer dimension (d) of 7.5 mm, and a holding dimension (b) of a value shown in Table 1 (see FIG. 5). Moreover, the minimum thickness (t) ranges from 2.3% to 36% of the maximum outer dimension (d).

Comparative Example

Figure 21:
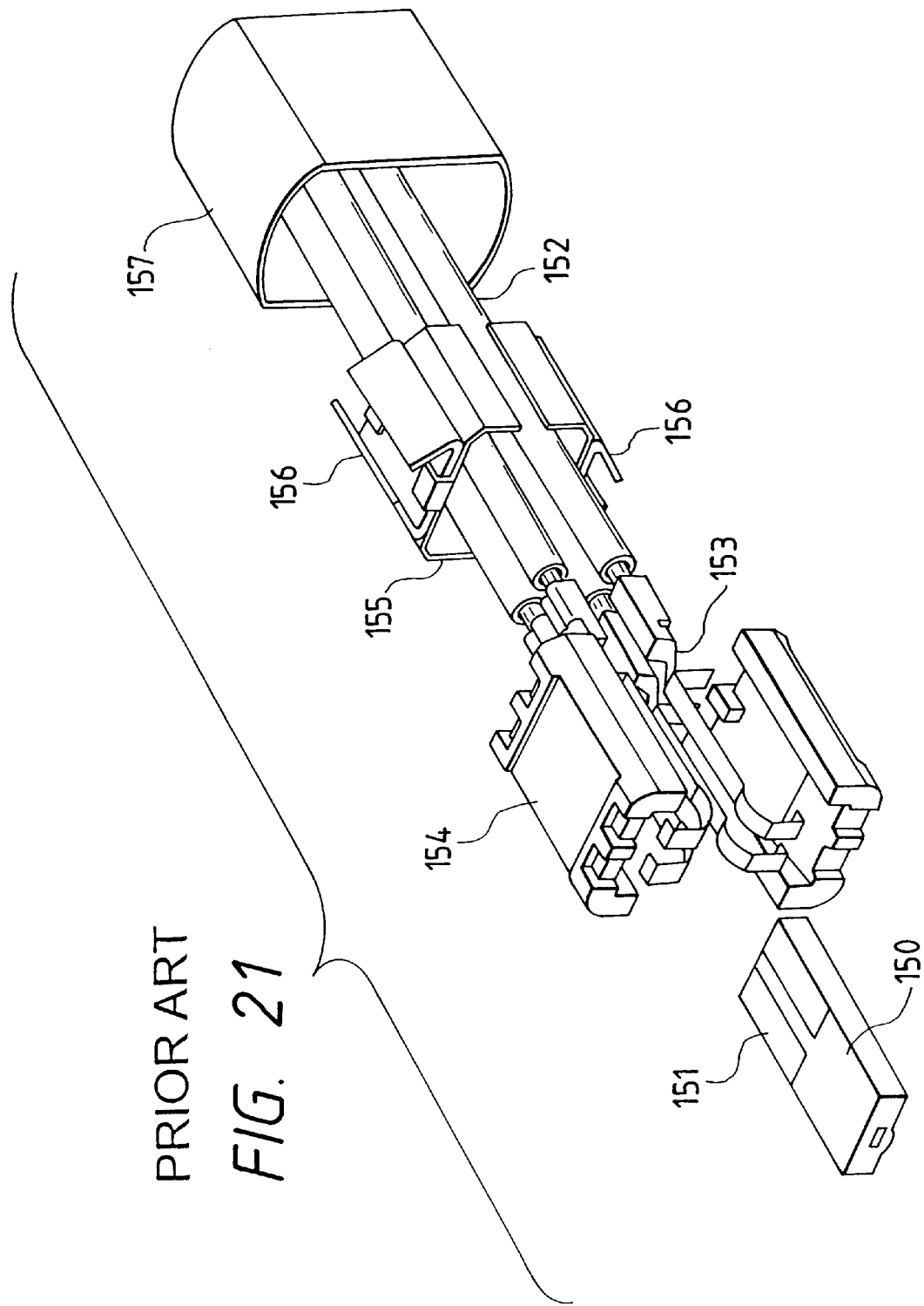
FIG. 21 is a perspective decomposed view of a conventional terminal to be used in a conventional electronic ceramic component in high temperature use.

The connection unit 10 (the ceramic element 2, the conductive wires 153 (male contacts), and the insulating plates 9) basically composed of a pressing spring 156, a fixing metal fitting 155, a ceramic housing 154, and the like are shown in FIG. 21 (a structure in which spring force is used to clamp the lead wire 8). The pressing spring 156 and a clamping ring 157 are made of stainless steel, Their minimum thicknesses are about 0.2 mm. The maximum outer dimension (d) of the clamping ring 157 is about 13 mm and the minimum thickness (t) is about 1.6% of the maximum outer dimension (d).

Figure 7:
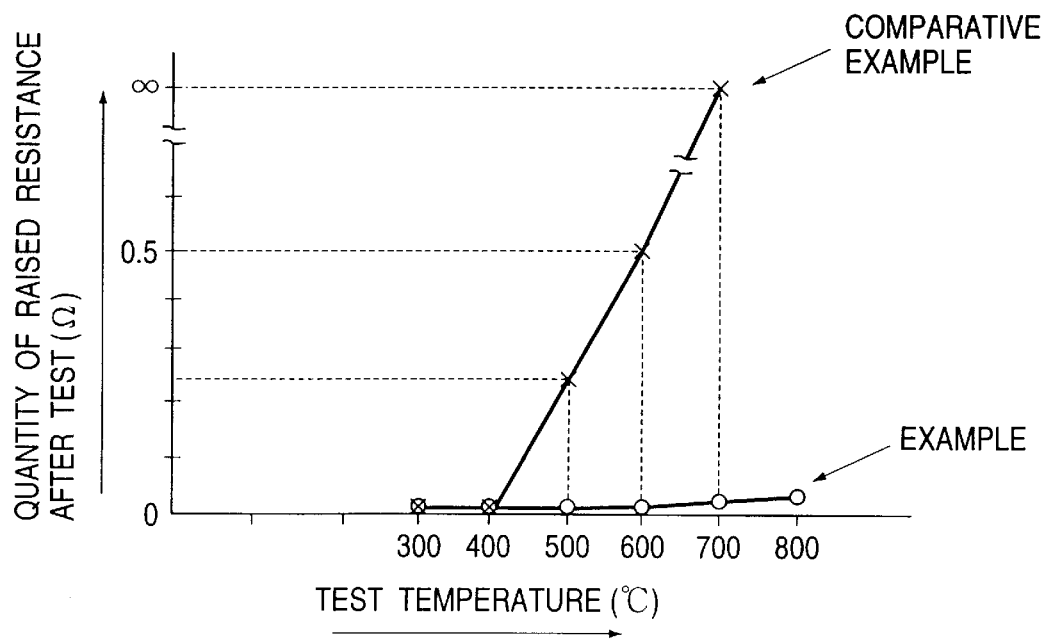
FIG. 7 is a graph showing contact resistance values risen from initial values, measured between a metal lead and an electrode portion of the ceramic elements after test based on a first experiment, as a function of temperature.

Each of the example and comparative example samples is formed in such a way that the metal ring 11 is attached to the connection unit 10 by press-fitting or rather pressure fitting. Six samples are used as each of the example samples and the comparative examples, after which the samples are exposed to 300° C., 400° C., 500° C., 600° C., 700° C., and 800° C. for 10,000 hours. Then, change in the contact resistance between the ceramic element 2 and the conductive wires 8 is measured. Results of the experiments are shown in FIG. 7.

TABLE 1

| | Experiment 1 | Example | Comp. Ex. |
|---|---|---|---|
| A | Ring metal fitting/ electrode | Incoloy 909/ Inconel 750 | Stainless/ Inconel 750 |
| | Min. thickness t (mm) | 0.705 | 0.200 |
| | Outer dimension d (mm) | 7.52 | 12.60 |
| | t/d | 0.094 | 0.016 |
| B | Dimension a (mm) | 3.601 | — |
| | Dimension b (mm) | 3.502 | — |
| | clamping interference δ (mm) (a-b) | 0.099 | — |
| C | Dimension a1 (mm) | 3.601 | — |
| | Dimension b1 (mm) | 3.502 | — |
| | Clamping interference δ1 (mm) (a1-b1) | 0.099 | — |
| | δ1/b1 | 0.02827 | — |
| D | Resistance raise after endurance test (Ω) | 0.03 (800° C.) | 0.25 (500° C.) |
| | Load required to separate electrode (kgf) | more than 1 kg | |
| | Evaluation | Good | Bad |
| | Note | heat resistivity; more than 800° C. | heat resistivity; 500° C. |

A: Material
B: Pre-connection
C: Post connection and decomposition
D: Result of evaluation test As can be understood from results of the experiments shown in FIG. 7, example samples encounter a slight change in the resistance value when the temperature is in a range from 300° C. to 800° C. The main reason for this can be considered that the structure, in which the metal ring 11 strongly holds the connection unit 10 until the temperature is raised to a high level of 800° C., maintains the close contact between the ceramic element 2 and the lead wire 8 and thus air in the contact portion is insulated. The foregoing effect is confirmed from a fact that no oxide film is observed in the close contact portion as a result of the precise examination of the close contact portion after the experiment.

On the other hand, the resistance value of the comparative example sample (the sample having the structure in which the conductive wires are pressed against the electrode terminal portions of the ceramic element by spring force) rapidly raises at about 500° C. Then, no electrical conductivity is obtained when the temperature in not lower than 700° C. The foregoing fact in caused from rise in the resistance value attributable to generation of an oxide film on the contact surface between the lead wire 8 and the ceramic element 2. That is, from the results of the first experiment, a fact is confirmed that the electrode connection structure of the ceramic element 2 according to the example can stably be used for a long time when the temperature is 800° C. or lower.

Second Experimental Example

Then, a metal ring 11 (samples according to the first and second comparative examples in the second experimental example) having the minimum thickness (t) which is smaller than 2.3% of the maximum outer dimension (d) and the metal ring 11 (samples according to first and second examples in the second experimental example) having the minimum thickness (t) in the range of 2.3% to 36% are used to measure the separation resistance of the lead wire 8 so that the force of the metal ring 11 for holding the connection unit 10 is measured. Note that the comparative example samples (for example, the first and second comparative example samples) are names for distinguishing general samples from preferred samples. Therefore, the comparative example sample does not indicate conventional part or a part which is not included in the scope of the present invention. That is, the expression as the "example sample" means a preferred sample. The foregoing fact is also applied to the third experimental example and following experimental examples.

In the foregoing performance test, the following elements are employed.

The ceramic element 2 is made of PSZ having a width of 4 mm and a thickness of 1.3 mm. The lead wire 8 is made of Incoloy Alloy 909 having a width of 1.5 mm and a thickness of 0.2 mm.

The insulation plate 9 is formed into a rectangular plate-like shape made of alumina, the insulation plate 9 having a width of 4 mm. The thickness is adjusted to satisfy the value shown in Table 2. The post-decomposition interference ($\delta1$) is made to be in the range of 0.23% to 9.3% of the post-decomposition holding dimension (b1).

The metal ring 11 is made of Incoloy Alloy 909 and having a maximum outer dimension (d) of 7.5 mm and a holding dimension b of 3.5 mm. The minimum thickness (t) is changed so that first and second comparative example samples and first and second example samples are manufactured.

The minimum thickness (t) of the sample according to the first comparative example is 0.15 mm (t/d: 0.020), the minimum thickness (t) of the second comparative example sample is 0.165 mm (t/d: 0.022), the minimum thickness (t) of the first example sample is 0.18 mm (t/d: 0.024) and the minimum thickness (t) of the second example sample is 0.70 mm (t/d: 0.093).

Each of the first and second comparative example samples and the first and second example samples are formed by assembling the metal ring 11 to the connection unit 10 by press-fitting as described in the example. In a state where the ceramic element 2 is fixed, tension is applied to the lead wire 8 to measure a load with which the lead wire 8 is separated. Thus, evaluation is performed whether or not problems arise in that the electrode is shifted or separated during handling. The lower limit for the evaluation to made to be 1 kgf. Results of the experiments are shown in Table 2.

Note that clamping interference ($\delta$) indicates a quantity obtained by subtracting the connection dimension (a) and the holding dimension (b) before the metal ring 11 is attached to the connection unit 10.

TABLE 2

| Experiment 2 | | Comp. Ex. 1 | Comp. Ex. 2 | Example 1 | Example 1 |
|---|---|---|---|---|---|
| A | King metal fitting/Electrode | Incoloy 909/Incoloy 909 | | | |
| | Min. thickness t (mm) | 0.150 | 0.165 | 0.180 | 0.700 |
| | Outer dimension d (mm) | 7.49 | 7.51 | 7.50 | 7.53 |
| | t/d | 0.020 | 0.022 | 0.024 | 0.093 |
| B | Dimension a (mm) | 3.603 | 3.598 | 3.601 | 3.597 |
| | Dimension b (mm) | 3.501 | 3.497 | 3.501 | 3.496 |
| | clamping interference $\delta$ (mm) (a-b) | 0.102 | 0.101 | 0.100 | 0.101 |
| C | Dimension a1 (mm) | 3.603 | 3.598 | 3.601 | 3.597 |
| | Dimension b1 (mm) | 3.501 | 3.497 | 3.501 | 3.496 |
| | Clamping interference $\delta1$ (mm) (a1-b1) | 0.102 | 0.101 | 0.100 | 0.101 |
| | $\delta1/b1$ | 0.02913 | 0.02888 | 0.02856 | 0.02869 |
| D | Load required to separate electrode (kgf) | 0.3 | 0.5 | 1.0 | 10.0 |
| | Evaluation | Bad | Bad | Good | Bad |
| | Note | | Lack of resistance of electrode against separation | | |

A: Material
B: Pre-connection
C: Post connection and decomposition
D: Result of evaluation test As shown in Table 2, the structure satisfying $0.0023 \leq t/d$ as has been employed in the first and second example samples causes the load required to separate the lead wire 8 to be 1 kgf or greater. Thus, a problem can be prevented which arises in a manufacturing process (a process, which is performed to complete manufacture of the oxygen sensor 1) after the metal ring 11 has been attached to the connection unit 10 in that the conductive wires 8 are separated or shifted.

On the other hand, if the t/d is smaller than 0.023 as is provided for the first and second comparative example sample, the conductive wires 8 is separated when the load is smaller than 1 kgf. To prevent separation or shift of the lead wire 8 in the manufacturing process which is performed after the metal ring 11 has been attached to the connection unit 10, it is preferable that t/d be made to be 0.0023 or more.

Third Experimental Example

Note that an experiment for confirming the upper limit for t/d is performed. The method of the experiment is the same as that according to the second experiment example, except for the shape of the ring metal fittings.

Inner dimensions of the ring metal fitting are made to be constant except for the maximum outer dimension (d) which is changed from 7.5 mm to 24 mm to change the minimum thickness (t) of the ring metal fitting from 0.7 mm to 8.95 mm. As a result, ring metal fittings respectively having t/d=0.093 to 0.373 are obtained. The obtained ring metal fittings are subjected to experiments, which are performed by the same method as that according to the second experiment example. Results are shown in Table 3.

TABLE 3

| Experiment 3 | | Example 1 | Example 2 | Example 3 | Comp. Ex. 1 | Comp. Ex. 2 |
|---|---|---|---|---|---|---|
| A | Ring metal fitting/Electrode | Incoloy 909/Incoloy 909 | | | | |
| | Min. thickness t (mm) | 0.700 | 5.950 | 6.950 | 7.950 | 8.950 |
| | Outer dimension d (mm) | 7.50 | 18.00 | 20.00 | 22.00 | 24.00 |
| | t/d | 0.093 | 0.331 | 0.348 | 0.361 | 0.373 |
| B | Dimension a (mm) | 3.603 | 3.599 | 3.598 | 3.601 | 3.597 |
| | Dimension b (mm) | 3.501 | 3.501 | 3.497 | 3.501 | 3.496 |
| | clamping interference $\delta$ (mm) (a-b) | 0.102 | 0.098 | 0.101 | 0.100 | 0.101 |
| C | Dimension a1 (mm) | 3.603 | 3.599 | 3.598 | 3.601 | 3.597 |
| | Dimension b1 (mm) | 3.501 | 3.501 | 3.497 | 3.501 | 3.496 |
| | Clamping interference $\delta 1$ (mm) (a1-b1) | 0.102 | 0.098 | 0.101 | 0.100 | 0.101 |
| | $\delta 1/b1$ ($\times 10^{-2}$) | 2.913 | 2.799 | 2.886 | 2.856 | 2.889 |
| D | Load required to separate electrode (kgf) | 10.0 | 24.0 | UP 26.5 | 0.5 | 0.4 |
| | Evaluation | Good | Good | Good | Bad | Bad |
| | Note | | | E | F | F |

A: Material
B: Pre-connection
C: Post connection and decomposition
D: Result of evaluation test
E: Electrode is broken when load is 26.5 kgf. Connection portion withstood.
F: Alumina insulating plate is broken. Lack of resistance of electrode against separation As can be understood from Table 3, when the minimum thickness (t) of the ring metal fitting is enlarged, the rigidity of the ring metal fitting is enlarged. Thus, the resistance of the electrode against separation is raised. If t/d exceeds 35%, the rigidity is enlarged excessively. In this case, the residual stress which acts when the ring metal fitting attached is enlarged, thus causing the element, such as the alumina insulating plate, to easily be broken. To prevent frequent occurrence of the foregoing problem, it is preferable that t/d be 0.35 or less.

Fourth Experimental Example

Then, experiments are performed in which upper and lower limits for the post-decomposition interference ($\delta 1$) (a1–b1) obtained by subtracting post-decomposition holding dimension (b1) from post-decomposition connection dimension (a1) are confirmed.

Specifically, samples are used which had the post-decomposition interference ($\delta 1$) which is smaller than 0.23% of the post-decomposition holding dimension (b1) (samples according to first to second comparative examples in a fourth experimental examples), the post-decomposition interference ($\delta 1$) which is not less than 0.23% nor more than 9.3% of the post-decomposition holding dimension (b) (samples according to first to fourth examples in the fourth experimental example) and the post-decomposition interference ($\delta 1$) which is larger than 9.3% of the post-decomposition holding dimension (b) (a sample according to a third comparative example in the fourth experimental example). Thus, the resistance of the lead wire 8 from separation is measured so that the force of the metal ring 11 for holding the connection unit 10 is measured.

In the foregoing performance test, the following elements are used.

The ceramic element 2 is made of PSZ having a width of 4 mm and a thickness of 1.3 mm. The conductive wires 8 are made of SUS304 having a width of 1.5 mm and a thickness of about 0.2 mm. The metal ring 11 is made of SUS304 and arranged to have the minimum thickness (t) of 0.7 mm, the maximum outer dimension (d) of 7.5 mm and the holding dimension (b) of 3.5 mm (refer to FIG. 8) such that the minimum thickness (t) satisfies a range not less than 2.3% nor more than 36%.

The insulating plate 9 is formed into a rectangular plate-like shape made of alumina and having a width of 4 mm and the clamping interference ($\delta$) which is adjusted by changing the thickness. That is, the thickness of the insulation plate 9 is adjusted so that samples according to first to second comparative examples and satisfying $\delta 1/b1 < 0.2\%$, samples according to first to fourth examples and satisfying $0.23\% \leq \delta 1/b1 \leq 9.3\%$ and a sample according to a third comparative example and satisfying $\delta 1/b1 < 9.3\%$ are manufactured. Specifically, the sample according to the first comparative example satisfies $\delta 1/b1$: 0.0014 (rounded off to four decimal place similarly to the description below), the sample according to the second comparative example satisfies $\delta 1/b1$: 0.0023, the sample according to the first example satisfies $\delta 1/b1$: 0.0029, the sample according to the second example satisfies $\delta 1/b1$: 0.0288, the sample according to the third example satisfies $\delta 1/b1$: 0.0538, the sample according to the fourth example satisfies $\delta 1/b1$: 0.0902, and the sample according to the third comparative example satisfies $\delta 1/b1$: 0.0937.

Each of the samples according to the first to third comparative examples and the first to fourth examples is obtained by attaching the metal ring 11 to the connection unit 10 by press-fitting. Two samples are manufactured for each example so that either of the two samples is decomposed to confirm the post-decomposition interference ($\delta 1$) and the other sample is used to measure the load with which the lead wires 8 is separated. The method of the foregoing experiments is similar to that according to the second example. The criterion for the evaluation is determined such that 1 kgf is made to be the lower limit similarly to the second experimental example. Results of the experiments are shown in Table 4.

TABLE 4

| Experiment 4 | Comp. Ex. 1 | Comp. Ex. 2 | Ex. 1 | Ex. 2 | Ex. 3 | Ex. 4 | Comp. Ex. 1 |
|---|---|---|---|---|---|---|---|
| A Ring metal fitting/Electrode | | | SUS304/SUS304 | | | | |
| Min. thickness t (mm) | 0.702 | 0.699 | 0.704 | 0.701 | 0.700 | 0.697 | 0.699 |
| Outer dimension d (mm) | 7.52 | 7.48 | 7.49 | 7.50 | 7.48 | 7.52 | 7.51 |
| t/d | 0.093 | 0.093 | 0.094 | 0.093 | 0.094 | 0.093 | 0.093 |
| B Dimension a (mm) | 3.506 | 3.505 | 3.511 | 3.606 | 3.701 | 3.871 | 4.001 |
| Dimension b (mm) | 3.501 | 3.497 | 3.501 | 3.501 | 3.497 | 3.502 | 3.495 |
| clamping interference δ (mm) (a-b) | 0.005 | 0.008 | 0.010 | 0.105 | 0.204 | 0.369 | 0.505 |
| C Dimension a1 (mm) | 3.506 | 3.505 | 3.511 | 3.606 | 3.701 | 3.869 | 3.992 |
| Dimension b1 (mm) | 3.501 | 3.497 | 3.501 | 3.505 | 3.512 | 3.549 | 3.6501 |
| Clamping interference δ1 (mm) (a1-b1) | 0.005 | 0.008 | 0.010 | 0.101 | 0.189 | 0.320 | 0.342 |
| δ1/b1 (× $10^{-3}$) | 0.143 | 0.229 | 0.286 | 2.882 | 5.382 | 9.017 | 9.370 |
| Load required to separate electrode (kgf) | 0.5 | 0.8 | 1.0 | 11.0 | 23.0 | up 26.0 | 0.8 |
| Evaluation | Bad | Bad | Good | Good | Good | Good | Bad |
| Note | F | F | | | | E | G |

A: Material
B: Pre-connection
C: Post connection and decomposition
D: Result of evaluation test
E: Electrode is broken when load is 26 kgf. Connection portion withstood.
F: Alumina insulating plate is broken. Lack of resistance of electrode against separation
G: Parts are broken. Lack of resistance of electrode against separation As shown in Table 4, the structure according to the first to fourth examples in which 0.23%≦δ1/t1≦9.3% causes the load required for the lead wire 8 to be separated to be 1 kgf or greater. Thus, the problem can be prevented which arises in a manufacturing process (a process, which is performed to complete manufacture of the oxygen sensor 1) after the metal ring 11 has been attached to the connection unit 10 in that the lead wires 8 are separated or shifted. On the other hand, when δ1/b1<0.23% as in the first and second comparative examples, the load required for the lead wire 8 to be separated is made to be smaller than 1 kgf. To lower the possibility in the manufacturing process (the process, which is performed to complete manufacture of the oxygen sensor 1) after the metal ring 11 has been attached to the connection unit 10 in that the lead wires 8 are separated or shifted, it is preferable that δ1/t1≧0.23%.

When δ1/b1<9.3% as in the third comparative example, the elements (the insulation plate 9 in the experiment) of the connection unit are broken and lead wire 8 is separated with the load smaller than 1 kgf, To prevent the possibility of the foregoing breakage, it is preferable that δ1/b1≦9.3%.

Fifth Experimental Example

Since the ceramic element 2 for use in the oxygen sensor 1 is exposed to exhaust gas and thus heated as described in the above-mentioned embodiments, a proper holding force must be maintained even at the highest temperature (Tm) for use, Therefore, an experiment is performed to confirm the lower limit for the interference (δm) at the highest temperature between the connection dimension (am) and the holding dimension (bm) at the highest temperature (Tm) permitted for the ceramic element 2 to be used.

Specifically, samples having an interference (δm) at the highest temperature of 0.1% or more (samples according to first and second examples in the fifth experimental example) and samples having an interference (δm) at the highest temperature of less than 0.1% (samples according to first and fourth comparative examples in the fifth experimental example) are used to measure the separation resistance of the lead wire 8 in a case where the highest temperature for use is set to be 600° C. so that the force of the metal ring 11 for holding the connection unit 10 is measured.

In the foregoing performance test, the following elements are employed.

The ceramic element 2 is made of PSZ having a width of 4 mm and a thickness of 1.3 mm. The lead wire 8 is made of SUS304 having a width of 1.5 mm and a thickness of about 0.2 mm.

The metal ring 11 is made of SUS304 having a minimum thickness (t) of 0.7 mm, a maximum outer dimension (d) of 7.5 mm and a holding dimension (b) of 3.5 mm (see FIG. 2). Moreover, the minimum thickness (t) satisfies 2.3% or more of the maximum outer dimension (d).

The insulating plate 9 is made of alumina formed into a rectangular plate-like shape having a width of 4 mm. The clamping interference (δ) is adjusted by changing the thickness. That is, the thickness of the insulating plate 9 is adjusted so that samples according to first and second examples and satisfying δm/bm≧0.1% and samples according to first and second comparative examples and satisfying δm/bm<0.1% are manufactured.

Each of the samples according to the first and second examples and the first and second comparative examples is formed by clamping the metal ring 11 to the connection unit 10 by shrink-fitting (only the metal ring 11 is heated to 600° C. to expand the same, after which the metal ring 11 is connected to the connection unit 10, and then the elements are cooled). The samples are exposed to endurance tests in which the elements are exposed at 600° C. for 10,000 hours in the atmosphere, and then change in the resistance value between the ceramic element 2 and the lead wire 8 is measured. Then, the metal ring 11 is removed from the connection unit 10, and then the post-decomposition interference (δ1) is measured. Results of the measurement, the dimensions of each element (the ceramic element 2, the lead wire 8, the insulation plate 9 and the metal ring 11) and the thermal expansion coefficients are used to calculate the interference (δm) at the highest temperature at the highest temperature (600° C.) for use.

The sample according to the first example satisfies δm/bm: 0.0026 (rounded off to four decimal place similarly to the description below and applied to the description hereinafter), the sample according to the second experiment satisfies δm/bm: 0.0011, the sample according to the first comparative example satisfies δm/bm: 0.0009, and the sample according to the second comparative example satisfies δm/bm: 0,0006. Results of the fifth experimental example are evaluated in accordance with the criteria shown in Table 1. Results of the fifth experimental example are shown in Table 5.

TABLE 5

|   | Experiment 5 | Example 1 | Example 2 | Comp. Ex. 1 | Comp. Ex. 2 |
|---|---|---|---|---|---|
| A | King metal fitting/Electrode | SUS304/SUS304 | | | |
|   | Min. thickness t (mm) | 0.702 | 0.699 | 0.704 | 0.697 |
|   | Outer dimension d (mm) | 7.52 | 7.51 | 7.49 | 7.50 |
|   | t/d | 0.093 | 0.093 | 0.094 | 0.093 |
| B | Dimension a (mm) | 3.523 | 3.522 | 3.517 | 3.517 |
|   | Dimension b (mm) | 3.497 | 3.501 | 3.497 | 3.498 |
|   | clamping interference δ (mm) (a-b) | 0.026 | 0.021 | 0.020 | 0.019 |
| C | Dimension a1 (mm) | 3.523 | 3.522 | 3.517 | 3.517 |
|   | Dimension b1 (mm) | 3.497 | 3.501 | 3.497 | 3.498 |
|   | Clamping interference δ1 (mm) (a1-b1) | 0.026 | 0.021 | 0.020 | 0.019 |
|   | δ1/b1 (× 10$^{-2}$) | 0.743 | 0.600 | 0.572 | 0.543 |
| D | am dimension (mm) | 3.544 | 3.543 | 3.538 | 3.538 |
|   | bm dimension (mm) | 3.535 | 3.539 | 3.535 | 3.536 |
|   | Interference δm (mm) (a2-b2) | 0.009 | 0.004 | 0.003 | 0.002 |
|   | δm/bm | 0.00255 | 0.00113 | 0.00065 | 0.0005 |
| E | Rise in resistance after endurance test (Ω) | 0.1 | 0.2 | 0.5 | ∞ |
|   | Load | 1 kg or | 1 kg or | — | — |
|   | required to separate electrode (kgf) | greater | greater | | |
|   | Evaluation | Good | Good | Bad | Bad |
|   | Note | | | F | F |

A: Material
B. Pre-connection
C: Post connection and decomposition
D: Highest temperature part (calculated from post connection and decomposition dimension)
E: Result of evaluation test
F: Resistance is raised excessively. (Heat resistance unsatisfactory)

As can be understood from the results of the experiments shown in Table 5, the structures according to the first and second examples in which δm/bm≧0.1% is able to lower the resistance value to be 0.2Ω or lower and thus rise in the resistance value of the contact portion can be prevented. The reason for this can be estimated that the structure, in which δm/bm 0.1%, enables the metal ring 11 to strongly hold the connection unit 10 even at the high temperature of 600° C. and thus causes the contact between the ceramic element 2 and the lead wire 8 to be maintained to prevent air in the contact portion to be insulated.

On the other hand, in the first and second comparative examples in each of which δm/bm<0.1%, an estimation is performed that the force of the metal ring 11 for holding the connection unit 10 is reduced at the high temperature of 600° C., thus air is introduced into the contact portion between the ceramic element 2 and the lead wire 8 and an oxide film is formed on the surface of the lead wire 8 resulting in that the resistance value being raised. To prevent rise in the resistance value, it is preferable that δm/bm≧0.1%.

Sixth Experimental Example

In an example case of a sensor for a vehicle, the oxygen sensor is thermally fatigued because of the environment for use in which start and stop are repeated. Therefore, the following samples (samples according to a comparative example and first to third examples) are subjected to thermal cycle tests in which the temperature is repeated between the room temperature and a hot level (200° C. to 800° C.) by 1000 cycles. Specifically, a cycle in which each sample is heated for 30 minutes in a heating furnace and the sample is forcibly cooled on the outside of the furnace for 30 minutes is repeated 1000 times. After the test is completed, change in the contact resistance is measured at the room temperature, and then the sample is again heated to the highest temperature in the test to measure the load required to separate the electrode.

The material of the electrode is Waspaloy Alloy (trade name), that of the insulation member is alumina and the following materials are employed to form the ring metal fitting. By using an element having an initial clamping interference of 0.1 mm, press-fitting is performed so that a connection unit is obtained.

Materials of Ring Metal Fitting

Figure 18:
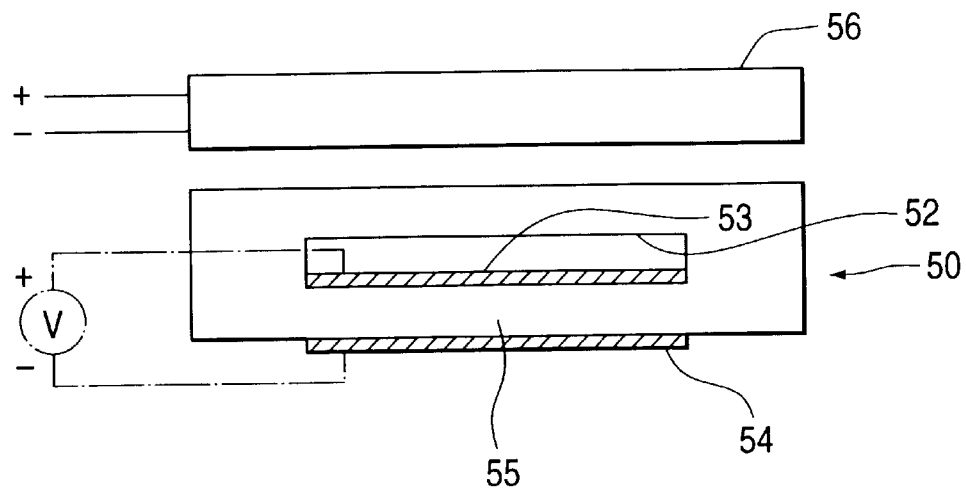
FIG. 18 is a schematic diagram of another oxygen sensor having a zirconia ceramic element forming a oxygen concentrating cell with electrode portions formed therein, to which the present invention is applicable.

Comparative Example: SUS304 (conventional element: FIG. 18)

First Example: Incoloy Alloy 909 (low expansion metal/age-hardening element . . . age-hardening temperature: 720° C.)

Second Example: Waspaloy Alloy (excellent heat-resisting alloy . . . age-hardening temperature: 843° C.)

Third Example: Inconel Alloy 650 (excellent heat resisting alloy . . . non-age-hardening type metal)

Note that the compositions of the ring metal fittings are as shown in Table 6. Incoloy Alloy 909 is an iron-based low expansion metal, Waspaloy Alloy and Inconel Alloy 650 are Ni-based excellent heat-resisting alloys.

TABLE 6

| | Young's Modulus (kgf/mm$^2$) | Thermal Expansion Coefficient (room temp. to 500° C. | Composition |
| --- | --- | --- | --- |
| SUS 304 | 21000 | 18 × 10$^{-6}$ | Fe: balance; Cr: 18%; Ni: 8% |
| Incoloy 909 | 16000 | 8 × 10$^{-6}$ | Fe: balance; Ni: 38%; Co: 13%; Nb: 5%; Ti: 1% |
| Inconel 625 | 21000 | 14 × 10$^{-6}$ | Ni: balance; Cr: 22%; Mo: 9%; Fe: 3%; Nb + Ta: 4% |
| Waspaloy | 21000 | 14 × 10$^{-6}$ | Ni: balance; Cr: 19%; Co: 14%; Mo: 4%; Ti: 3% |

(Results of Experiments)

Figure 9:
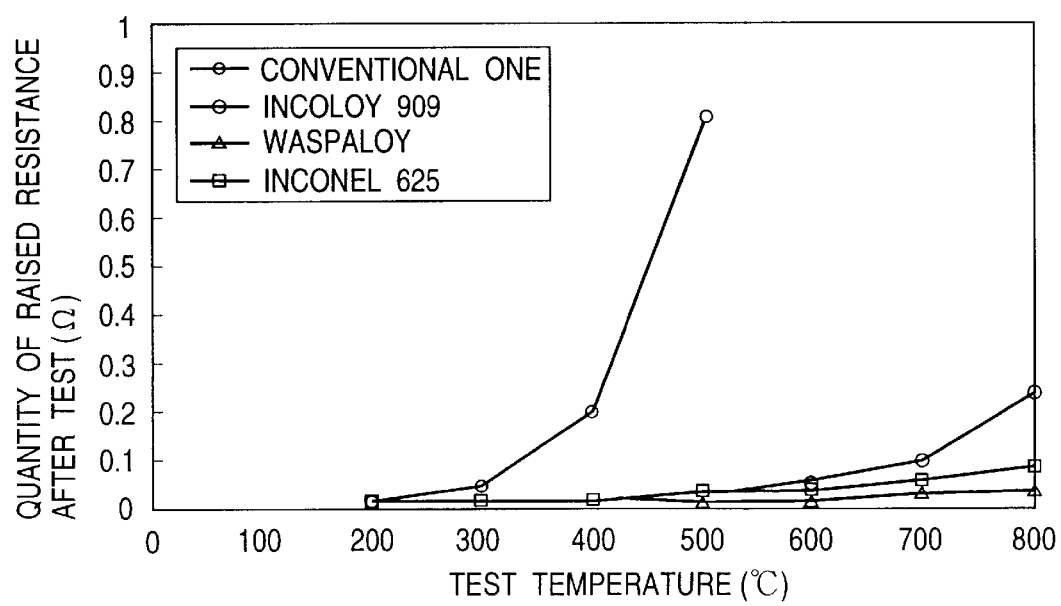
FIG. 9 is a graph showing contact resistance values risen from initial values, measured between a metal lead and an electrode portion of the ceramic elements after test based on a second experiment, as a function of temperature.

Although the sample (the conventional one) according to the comparative example is confirmed in the first experimental example (maintained at high temperatures) to have heat resistance up to 500° C. (the quantity of rise in the resistance: about 0.25Ω), the heat resistance is, in this experiment, lowered to 400° C. as shown in FIG. 9. Thus, a severe result is obtained as compared with the high temperature maintained experiment according to first and fourth experimental examples.

Figure 10:
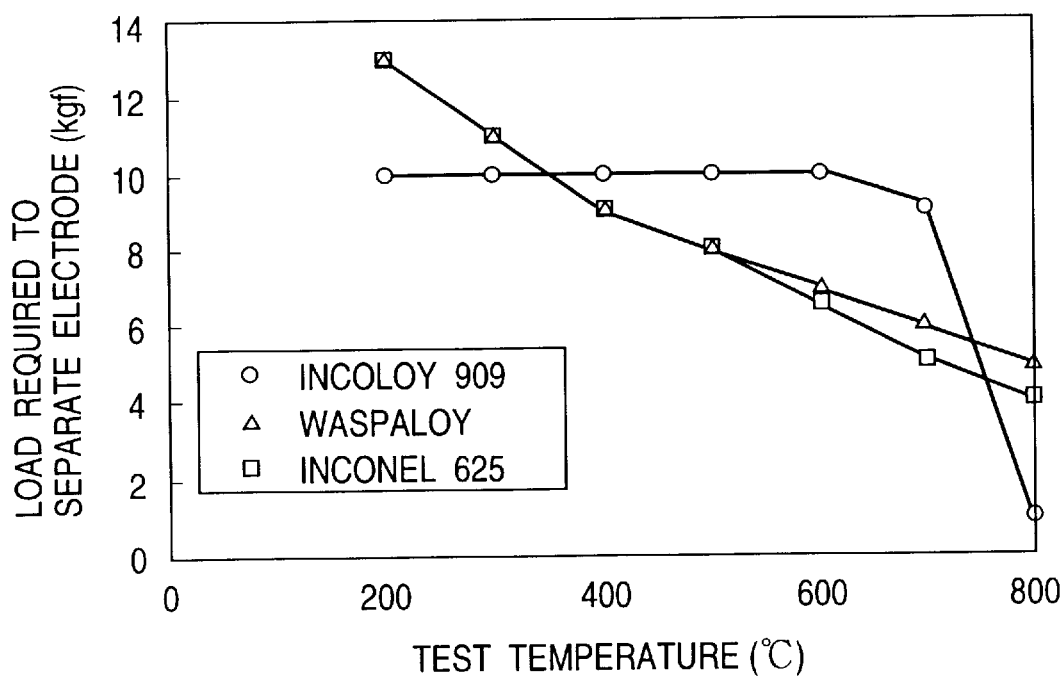
FIG. 10 is a graph showing a load required for pulling a metal lead off from an electronic component sample based on a second experiment, as a function of temperature.

When the ring metal fitting according to the first example and made of Incoloy Alloy 909 is employed, the heat resistance to 800° C. in confirmed similarly to the first embodiment (maintained at high temperatures) as shown in FIG. 9. As shown in FIG. 10, the resistance against separation of the electrode is lowered at 800° C. The reason for this can be considered that the Incoloy Alloy 909, subjected to the age-hardening hardening process (maintained at 720° C. for 8 hours and 620° C. for 8 hours) to improve the resistance before the press-fitting process is performed, encounters excess age-hardening, thus causing the durability to deteriorate when the test temperature exceeded 720° C. (the age-hardening temperature).

In a case where the ring metal fitting according to the second example and made of Waspaloy Alloy is employed, the heat resistance to 800° C. or higher is resulted in this experiment. Although the resistance of the electrode against separation at 400° C. to 700° C. is inferior to that of Incoloy Alloy 909, the reason for this is that its thermal expansion coefficient larger than that of Incoloy Alloy 909, which is low expansion metal, causes the clamping interference to be reduced when the temperature is raised. Since Waspaloy Alloy has a high age-hardening temperature of 843° C. and therefore generation of excess age-hardening can be prevented, excess deterioration in the resistance of the electrode against separation does not take place even at 800° C.

Also in the case where the ring metal fitting made of Inconel Alloy 625 according to the third example is used, the heat resistance in this experiment is 800° C. or higher. Although deterioration in the durability occurring attributable to excess age-hardening does not raise a problem because Inconel Alloy 625 is non-age-hardening type metal, also improvement in the durability cannot be realized even if the age-hardening process is performed. Accordingly, a roll hardening process is performed to improve the durability. Although the resistance of the electrode against separation is inferior to that of Incoloy Alloy 909 at 400° C. to 700° C. similarly to Waspaloy Alloy, large resistance is realized at 800° C. and thus inversion takes place.

Figure 8:
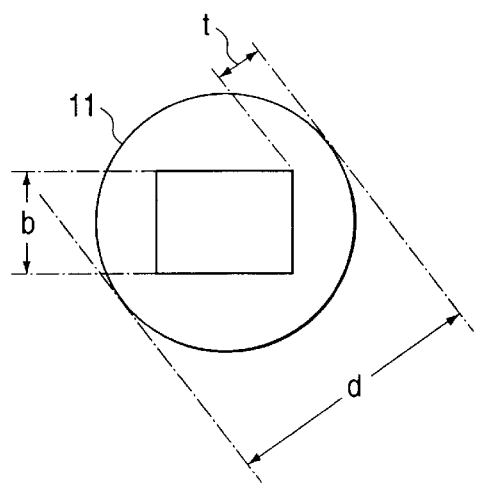
FIG. 8 is a plan view of another thermal resistant ring for pressure or shrink fitting, designed according to the invention.

Although the above-mentioned embodiment has been described about a structure in which the metal ring 11 is formed into a rectangular and tubular shape, the metal ring 11 may have a structure in which the outer shape is made to be a circular shape and a through hole in the form of a rectangular shape, for example, a square is formed in the inner central portion, as shown in FIG. 8. In this case, the metal ring 11 shown in FIG. 6 may be attached to the inner portion of the outer cylindrical metal fitting 5 in the form of a cylindrical shape. That is, the outer cylindrical metal fitting 5 in the form of a cylindrical shape may be extended to fit to cover the metal ring 11 having a circular outer surface.

Although the above-mentioned description has been performed about the structure in which the ceramic element is used as the sensor, the present invention may be applied to a ceramic heater.

Figure 11:
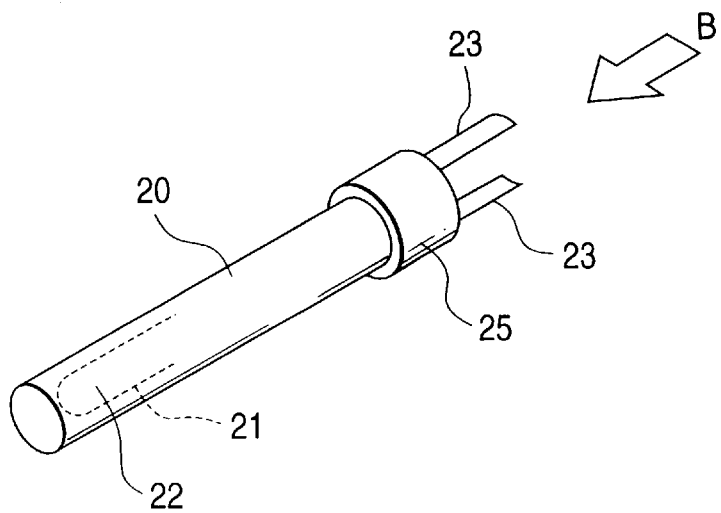
FIG. 11 is a perspective view of another electronic component assembly having metal leads unitarily assembled with a cylindrical ceramic element by a shrink or pressure fit, embodied according to the invention.

FIG. 11 shows an example of the foregoing structure. In a ceramic heater element 20, a heat-generating resistance wire 21 is embedded in the form of a U-shape having a turning point. A top end portion of the element 20 is formed into a heat generating portion 22. Electric power is directly or through an intermediate conductive wire, supplied to the heat-generating resistance wire 21 through two lead wires 23 serving as electrodes. The lead wires 23 are, by a ring metal fitting 25 formed into a cylindrical shape, clamped to electrode terminal portions, which are electrical connection portions of the element 20, so that electrical conduction is realized.

Figure 12:
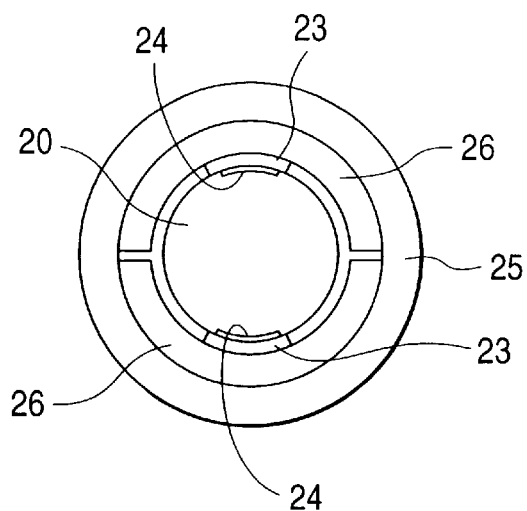
FIG. 12 is a view of the end of the electronic component assembly, viewed from the position indicated by an arrow B of FIG. 11.

As shown in FIG. 12, two electrode terminal portions 24 are, apart from each other for a predetermined distance (symmetrically with respect to the center in this example), formed on the outer surface of the ceramic heater element 20. Then, the lead wires 23 in the form of thin plate-like shapes are in contact with the electrode terminal portions 24. The two lead wires 23 are curved into circular-arc shapes each having a curvature which enables the lead wires 23 to be disposed along the outer surface of the heater element 20 in the clamped state. Two insulating plate 26, each having a circular-arc cross sectional shape corresponding to the outer surface of the ceramic heater element 20, are stacked on the foregoing elements from outside. Moreover, the ring metal fitting 25 in the cylindrical form is attached to the foregoing elements from outside by close-fitting. In this case, each of the insulating plates 26 is formed into a shape obtained by dividing a cylinder into two portion in the axial direction. The insulating plates 26 are placed opposite to each other surrounding the ceramic heater element 20. The ring metal fitting 25 clamps each of the lead wires (electrode plates) 23 to the electrode terminal portions 24 through the insulating plates 26. Namely, each of the lead wires 23 is maintained at a state where it is held between the electrode terminal portion of the ceramic heater element 20 and the insulating plates 26.

Seventh Embodiment

Figure 13A:
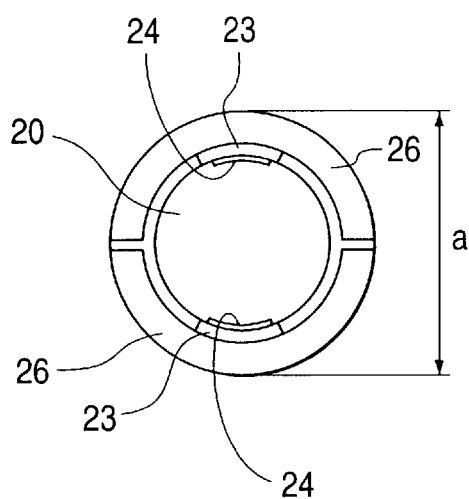
Figure 13B:
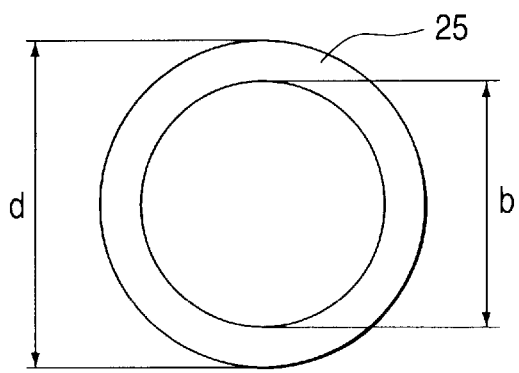
Figure 14:
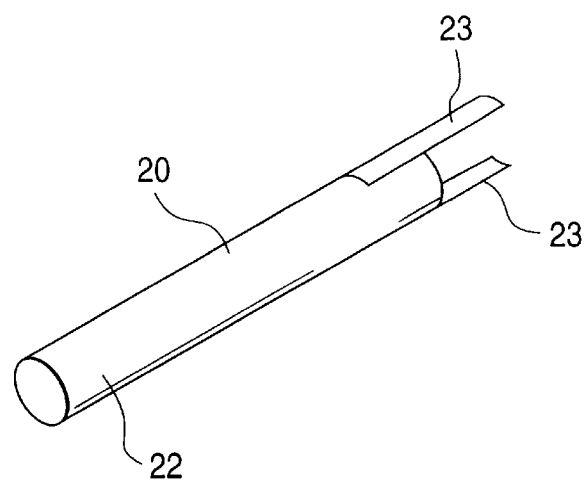
FIG. 14 is a perspective view of the cylindrical ceramic element with the metal leads placed thereon, as indicated in FIG. 13 A.

In a ceramic heater formed into a solid cylindrical shape (having a diameter of 4 mm and a length of 40 mm) and made of silicon nitride, an element according to the present invention (see FIGS. 13A to 13B) and an element according to a comparative example (see FIG. 14) are shown. The ceramic heater according to this embodiment has a W wire (tungsten wire) having a diameter of 0.4 mm embedded therein. Two electrical connection portions, consisting of positive and negative polarity portions, are exposed to the outside. Ni-plating having a thickness at 2 μm is applied to the surface of the electrical connection portions in order to prevent oxidation of tungsten.

EXAMPLE

The ring metal fitting 25 made of Incoloy Alloy 909 is formed into a cylindrical shape having an outer diameter (d) of 10 mm and an inner diameter (b) of 6 mm. The insulating plates 26 is formed into a semi-cylindrical shape made of alumina. The lead wires (electrodes) 23 are made of Inconel Alloy 750 having a thickness of 0.25 mm. A clamping interference of 50 μm is realized by combining the above-mentioned elements, and then lubricant is applied to the inner surface of the ring metal fitting 25, after which connection is established by press-fitting. Also the cylindrical ring metal fitting 25 is provided with a tapered inner surface 11b in the form of a circular cone at the end portion at which press-fitting is started as shown in FIG. 6 indicating the position of the tapered inner surface. On the other hand, a tapered outer surface 9a corresponding to the tapered inner surface and having a circular cone shape is provided for the portion in which the ceramic heater element 20 is press-fitted.

An electric current is allowed to flow in the conductive wires (the electrodes) 23 with 11 V by 20 A so that the top end of the ceramic heater is heated. The temperature of the electrode connection portion is stabilized to 500° C. after supplying the electric current for one minute. Then, the supply of the electric current is interrupted for 3 minutes to lower the temperature or the electrode connection portion to the room temperature. The above-mentioned ON-OFF durability test in performed by 100 cycles to 1000 cycles, and then change in the contact resistance is measured to evaluate the results.

Comparative Example

Conductive wires (electrodes) 23 having a thickness of 0.25 mm and made of Inconel Alloy 750 are, by brazing, directly connected to the ceramic heater element 20 (see FIG. 14) by using an eutectic brazing filler material made of AgCu (Ag=72%, Cu=28%, and melting point: 780° C.). The obtained sample is subjected to an ON-OFF durability test similar to that performed in the example.

Results of Experiments

The samples according to the example are free from defects even after 1000 cycles of the test are performed. On the other hand, the brazed portion of the sample according to the comparative example is broken after 200 cycles of the test are completed.

Although the above-mentioned description has been performed about the structure in which the ceramic heater is solely employed, the above-mentioned ceramic heater may be included in an oxygen sensor (for example, it is included in parallel or coaxially with the oxygen sensor).

Figure 15:
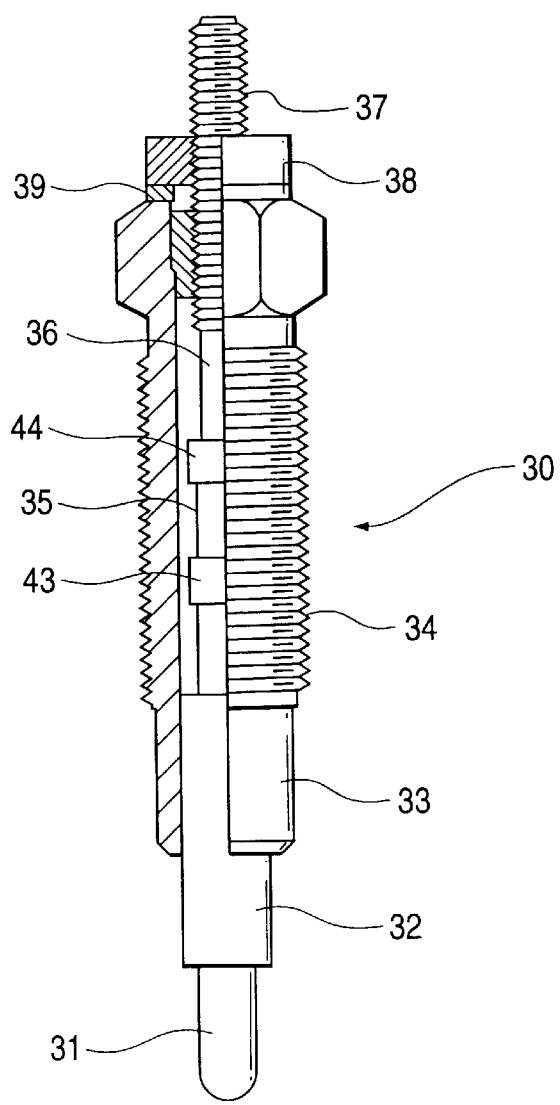
FIG. 15 is a partially cross sectional plan view of a glow plug having a ceramic heating element, to which the present invention is applicable.

Also the present invention may be applied to an electrode connection portion in a glow plug made of ceramic. FIG. 15 shows an example of a glow plug 30. A glow plug element 31 is held in a metal housing 33 through a metal sleeve 32 so that a thread portion 34 formed on the outer surface of the glow plug element 31 is fixed to an engine block (not shown). A heating portion in the glow plug 31 is supplied with electric power through a coil-shape lead wire 35 and a metal shaft 36. The metal shaft 36 having a nut 38 fitted to a thread portion 37 formed on the outer surface thereof is fitted to a metal housing 33 so that the lead wire 35 is coaxially fixed to the glow plug 31 and electrically insulated from the metal housing 33 by an insulation member 39.

Figure 16:
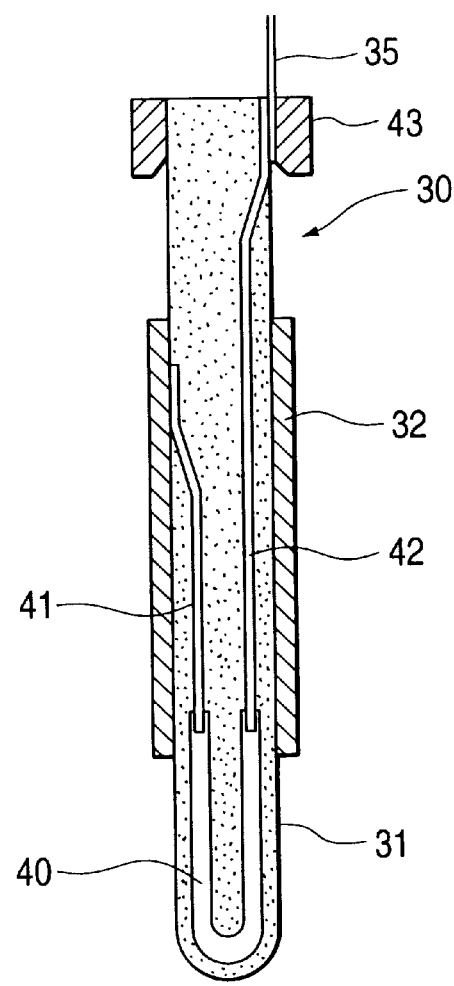
FIG. 16 is a cross sectional view of essential part of the glow plug shown in FIG. 15.

As shown in FIG. 16, the glow plug 30 includes a U-shape ceramic heat generating member 40 and embedded conductive wires 41 and 42 connected to the two ends of the ceramic heat generating member 40 and embedded in the glow plug 30. The embedded conductive wire 41 is grounded to the metal sleeve 32, while the embedded conductive wire 42 is connected to the conductive wire 35 by the ring metal fitting 43. An end of the embedded conductive wire 42 is exposed to the outside of the glow plug element 31 so as to be formed into the electrode connection portion. In a state where the conductive wire 35 is disposed in the electrode connection portion, the ring metal fitting 43 is fitted to an end of the glow plus 30 by close-fitting, such as press-fitting or shrink-fitting. Thus, an end of the conductive wire 35 is fixed to the electrode connection portion so that an electrically conductive state is maintained.

That is, the inner diameter of the ring metal fitting 43 is made to be smaller than an outer dimension (dimension in a connected state) obtained by adding the dimensions of the two elements forming the connection unit, that is, the outer diameter of the glow plug 31 and the thickness or the diameter of the lead wire 35. In this embodiment, no insulation plate is included and the ring metal fitting 43 is directly fixed to the lead wire 35. Note that another end of the conductive wire 35 may be connected to the metal shaft 36 by a proper method so that the other end of the conductive wire 35 is fixed to the outer surface of the metal shaft 36 by close-fitting of a ring metal fitting 44 similar to the above-mentioned structure. In either case, electric power is supplied to the ceramic heat generating member 40 through the metal shaft 36 and the conductive wire 35 and the embedded conductive wires 42 and 41 so that the ceramic heat generating member 40 red-heats. Also the ring metal fitting 43 having the above-mentioned structure is able to, as preferred values, employ the post-decomposition clamping interference, the ratio of the minimum thickness and the maximum outer dimension and the clamping interference at the highest temperature described in the above-mentioned embodiments.

Figure 17:
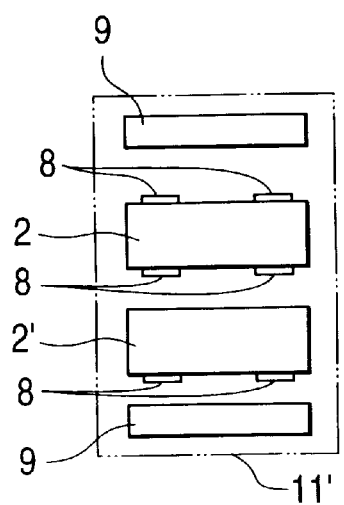
FIG. 17 is a schematic plan view of a stack of alumina and zirconia ceramic elements and electrodes formed therein forming a ceramic heater inside, to which the present invention is applicable.

As shown in FIG. 17, a multi-layered electrode connection structure may be employed in which a plurality of (for example, two) ceramic elements 2 and 2' are stacked and disposed and they are, if necessary, held by insulating plates 9 from two sides, and a metal ring 11' (only the inner surface is illustrated in the drawing) is used to close-fit the foregoing elements. In this case, for example, two electrode terminal portions are formed on each side of the ceramic element 2 so that four terminal electrode portions are formed and conductive wires 8 (electrode members) are formed. Thus, four electrode connection portions including the above-mentioned oxygen sensor and the heater are formed. Moreover, two electrode connection portions are provided for the electrode terminal portion of the ceramic element 2' to be the electrode connection portion for an NOx sensor. Thus, six combined electrode connection structures can be obtained in the above-mentioned case. In this case, the total sum of the two ceramic elements 2 and 2', two insulating plates 9, and three conductive wires is the total dimension (the dimension of the connection state) of the connection unit. The inner dimension of the ceramic elements 2 and 2' and the like of the metal ring 11' in the clamping direction is the holding dimension. Then, the holding dimension is made to be smaller than the connection dimension by setting the clumping interference as is performed in the foregoing embodiment. The other structure may be formed by the contents of the above-mentioned embodiments.

Although the above-mentioned embodiments have been described about the structure in which the ring metal fitting made of metal, that is, the metal ring 11 and the like are provided, the ring metal fitting may be made of ceramic, a sintered body of ceramic and a metal material or a combined material including resin and ceramic or metal depending upon the environment in which the ceramic element is used. In a cage where the ring metal fitting is made of a non-conductive material, the insulating plate shown in FIG. 4 is not required.

The oxygen element sensor, particularly, the concentration cell type, has been described as the representative of the ceramic element sensor. The concentration cell type and the pump type oxygen sensor has been described as the representative of the ceramic sensor. Although their structures have been known, some examples will be described below.

FIG. 18 shows the concentration cell type oxygen sensor, which is equivalent to the sensor as shown in FIG. 1. An atmosphere introduce chamber 52, a porous reference electrode 53 and a porous detection electrode 54 is formed in a ceramic element 50 made of an oxygen ion conductive solid electrolyte, such as zirconia ($ZrO_2$). The reference electrode contact to the atmosphere while the detection electrode 54 contact to exhaust gas, so that a concentration cell electromotive force corresponding to the oxygen concentration in the exhaust gas in a porous wall portion 55. This electromotive force is detected as a sensor output to detect the oxygen concentration of the exhaust gas. A heater 56 heats the wall portion 55 to raise its temperature above a desired level at the time of starting an engine to accelerate the ionization of oxygen. In this embodiment, the oxygen sensor has four electrodes of two electrodes of the concentration cell and two electrodes of the heater.

Figure 19:
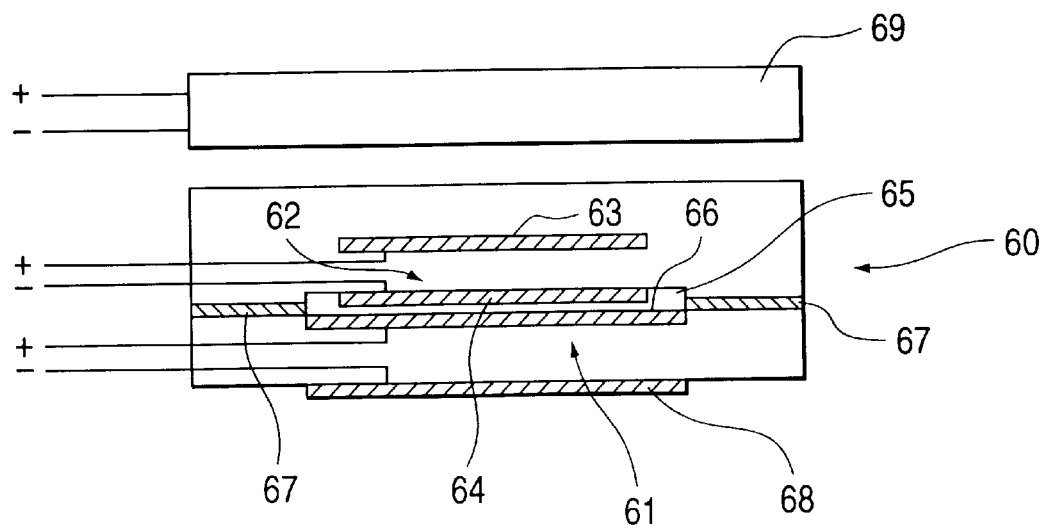
FIG. 19 is a schematic view of still another type of oxygen-sensor having a zirconia ceramic element forming a oxygen-pumping cell with electrode portions formed therein, to which the present invention is also applicable.

FIG. 19 shows a schematic diagram of the pump type whole area oxygen sensor. A ceramic element 60 is composed of an oxygen ion conductive solid electrode, and has a structure in which an oxygen pump element 61 is disposed to be opposite to an oxygen concentration cell element 62 while a measurement chamber 65 is arranged between the elements 61 and 62. The oxygen concentration cell element 62, which uses an electrode 63 embedded therein as an oxygen reference electrode, measures the oxygen concentration in the measurement chamber 65 by detecting the concentration cell electromotive force generated between itself and an electrode 64 on the side of the measurement chamber 65. On the other hand, a voltage is applied to an oxygen pump element 61 via electrodes 66 and 68 from an outer power source (not shown) so as to pump oxygen through an aperture 67 into or from the measurement chamber 65 at a velocity defined by the direction and the magnitude of the voltage. The operation of the oxygen pump element 61 is controlled by a controller (not shown) based on the oxygen concentration in the measurement chamber 65 detected by the oxygen concentration cell element 62 so that the oxygen concentration in the measurement chamber 65 is maintained in constant to correspond to the theoretical air fuel ratio. Then, the oxygen sensor according to this embodiment detects the air fuel ratio (A/F) of the exhaust gas based on the pump current of the oxygen pump element 61.

Generally, this type of oxygen sensor has six electrodes, i.e., two electrodes for detecting voltage, two electrodes for applying voltage to the oxygen pump element, and two electrodes for applying current to the heater 69. If two heaters are provided independently, the oxygen sensor has eight electrodes. In this case, for example, in FIG. 4, a group of three electrodes and another group of three electrodes are disposed on the opposite surfaces of the ceramic element 2, respectively. Then, each conductive wire 6 is arranged to each electrode. Thereafter, the metal ring 11 is clamped by shrink-fitting via the insulation plate 9. Alternatively, the oxygen sensor may have the structure as shown in FIG. 17.

Figure 20:
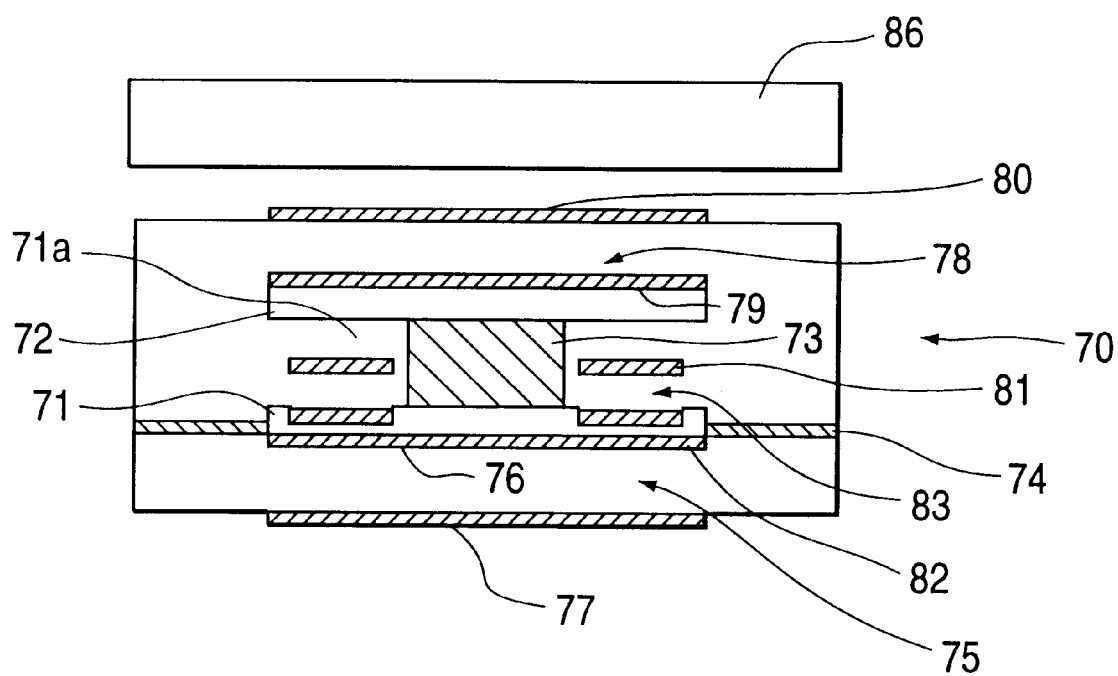
FIG. 20 is a schematic view of a Nox sensor having zirconia ceramic element with electrode portions formed therein, to which the present invention is applied.

Further, the present invention can be applied to the NOx sensor in addition to the oxygen sensor. FIG. 20 shows one example of a two-chamber type NOx sensor. A ceramic sensor element 70 is composed of the oxygen ion conductive solid electrolyte such as $ZrO_2$, in which a partition wall 71a is arranged between first and second measurement chambers 71 and 72 as well as the partition wall 71a is composed of a porous ceramic or the like so as to form second dispersion pores 73 therein to communicate the first and the second measurement chambers 71 and 72. The first measurement chamber 71 communicates with the circumference atmosphere via first dispersion pores 74. A first oxygen pump element 75 having electrodes 76 and 77 is arranged with respect to the first measurement chamber 71. A second oxygen pump element 78 having electrodes 79 and 80 is arranged with respect to the second measurement chamber 72. The arrangement position of the first oxygen pump element 75 is opposite to that of the second oxygen pump element 78 with respect to the partition wall 71a. An oxygen concentration cell element 83 is formed in the partition wall 71a which detects the oxygen sensor of the first measurement chamber 71. The oxygen concentration cell element 83 has an oxygen reference electrode 81 in the partition wall 71a and an opposite electrode 82 facing to the first measurement chamber 71.

The operation of the NOx sensor will be described. First, the circumference atmosphere gas is introduced into the first measurement chamber 71 via the first dispersion pores 74. Then, oxygen gas is pumped from thus introduced gas by the first oxygen pump element 75. Incidentally, the oxygen concentration in the measurement chamber is detected by the oxygen concentration cell element 83. Based on thus detected value, the operation of the first oxygen pump element 75 for pumping up oxygen is controlled by a controller (not shown) so that the oxygen concentration of the gas in the first measurement chamber 71 becomes a constant value at an extent where NOx is not analyzed. Thus, the gas in which oxygen is reduced moves to the second measurement chamber 72 via the second dispersion pores 73. In the second measurement chamber 72, the second oxygen pump element 78 pumps up oxygen to completely analyze NOx and oxygen in the gas. In this occasion, the concentration of NOx in the gas is detected based on the pump current of the second oxygen pump element 78.

Generally, this type of NOx sensor has four electrodes of two pairs of two electrodes for two oxygen pump elements 75 and 78, two electrodes for the oxygen concentration cell element 83, and two electrodes for the heater 86. If two heaters are provided independently, the NOx sensor has ten electrodes. This number of electrode terminal portions are formed on the ceramic element 70, and the conductive wires are press-fitted to respective electrode terminal portions by the ring metal fitting.

Incidentally, the present invention may be applied to another ceramic element, in addition to the oxygen sensor element, for example, an NOx sensor element, a CO sensor element, or a $CO_2$ sensor element. Moreover, the present invention may be applied to the ceramic heater element and the glow plug element as well as the sensor element, as described above.

What is claimed is:

1. A ceramic application electronic device for a vehicle which is used at high temperature, comprising:

a ceramic element which is formed so that an electrode terminal portion for connection with an electric circuit of said ceramic application electronic device formed therein is exposed to an outer surface thereof;

a conductive wire member which is attached to said electrode terminal portion so that said electrode terminal portion is electrically connected to an outside; and a ring member having a ring shape which surrounds a connection unit including said ceramic element and said conductive wire member from the outside and is clamped with said connection unit by shrink-fitting from the outside, while having a holding dimension, which is an inner dimension in a direction of the press-fitting of said conductive wire and said electrode terminal portion of said ceramic element, smaller than a connection dimension which is an outer dimension of said connection unit in the press-fitting direction of said conductive wire and said electrode terminal portion of said ceramic element.

2. A ceramic application electronic device according to claim 1, wherein said ring member is made of metal, and said connection unit further includes an insulation member for preventing direct contact of an inner surface of said ring member and said conductive wire member, said insulation member being disposed between said conductive member and said ring member.

3. A ceramic application electronic device according to claim 2, wherein said ring member comprises one of an age-hardening product of Fe-based ultra heat resistance alloy, an age-hardening product of Ni-based ultra heat resistance alloy, and a work hardening product of non-age-harding type of Ni-based heat resistant alloy.

4. A ceramic application electronic device according to claim 2, wherein said ring member is comprised of one selected from a group consisting of:

an alloy containing 1 to 40% by weight of Fe and a balance substantially consisting of Ni;

an alloy containing 1 to 30% by weight of Co and a balance substantially consisting of Ni;

an alloy containing 15 to 45% by weight of Cr and a balance substantially consisting of Ni;

an alloy containing 1 to 21% by weight of Fe and a balance substantially consisting of Co;

an alloy containing 10 to 20% by weight of Ni and a balance substantially consisting of Co;

an alloy containing 20 to 31% by weight of Cr and a balance substantially consisting of Co;

an alloy containing 2 to 43% by weight of Ni and a balance substantially consisting of Fe;

an alloy containing 3 to 23% by weight of Co and a balance substantially consisting of Fe; and an alloy containing 0.5 to 32% by weight of Cr and a balance substantially consisting of Fe.

5. A ceramic application electronic device according to claim 2, wherein a tapered inner surface is formed on an inner surface of an opening portion in an enter side of the shrink-fitting of said ring member to spread toward the outside, and a slant outer surface corresponding to said tapered inner surface is formed on an outer surface of an end portion of a side of said insulation material to which said ring member is press-fitted.

6. A ceramic application electronic device according to claim 1, wherein said ring member has a shape in which at least an inner surface is rectangular, and compressedly clamps said connection unit by an inner surface thereof.

7. A ceramic application electronic device according to claim 1, wherein said ceramic element has a columnar shape, and said ring member has a shape in which at least an inner surface is cylindrical and compressedly clamps said connection unit by an inner surface thereof.

8. A ceramic application electronic device according to claim 1, wherein when an assumption is made that the outer dimension of said connection member in the press-fitting direction of said ceramic element and the conductive wire is post-decomposition connection dimension a1, the inner dimension of said ring member in the press-fitting direction is post-decomposition holding dimension b1 (a1>b1) and the difference (a1−b1) between the post-decomposition connection dimension a1 and the post-decomposition holding dimension b1 is post-decomposition clamping interference $\delta$, post-decomposition interference $\delta$ is in the range of 0.23% to 9.3% of the post-decomposition holding dimension b1.

9. A ceramic application electronic device according to claim 8, wherein the post-decomposition interference $\delta$ is in the range of 1.5% to 4.5% of the post-decomposition holding dimension b1.

10. A ceramic application electronic device according to claim 1, wherein a minimum thickness of said ring member in a plan view of said ring shape is in the range of 2.3% to 35% of a maximum outer dimension of said ring metal fitting in the plan view of said ring shape.

11. A ceramic application electronic device according to claim 1, wherein when an assumption is made that a highest temperature at which said electrode connection structure is used is highest temperature Tm, the dimension of said connection member in the press-fitting direction of said ceramic element and said conductive wire is connection dimension am at the highest temperature, an inner dimension of said ring metal fitting in the press-fitting direction is holding dimension bm (am>bm) at the highest temperature and the difference am−bm between the connection dimension am at the highest temperature and the holding dimension at the highest temperature bm is an interference $\delta m$ at the highest temperature, the interference $\delta m$ at the highest temperature is not lower than 0.1% of the holding dimension bm at the highest temperature.

12. A ceramic application electronic device according to claim 1, wherein said ceramic application electronic device is one of an oxygen sensor device, an NOx sensor device, a CO sensor device, a $CO_2$ sensor device, ceramic heater device, and a ceramic glow plug.

13. A ceramic application electronic device according to claim 1, wherein said ceramic application electronic device is a ceramic gas sensor for detecting a concentration of a specific component in exhaust gas of a vehicle.

14. A ceramic application electronic device according to claim 13, wherein said electrode terminal portion of said ceramic element is electrically connected to a detection mechanism for detecting the concentration of a specific component in exhaust gas.

15. A ceramic application electronic device according to claim 13, further comprising:

an electric insulation member disposed at an outside of said conductive wire member; and a housing for housing said ring member, said insulation member, said conductive member and said ceramic element therein;

wherein said electrode terminal portion of said ceramic element is electrically connected to a detection mechanism formed therein for detecting the concentration of a specific component in exhaust gas, and said ring member maintains a condition where said insulation member is compressedly disposed between said ring member and said conductive wire member.

16. A ceramic application electronic device according to claim 13, wherein:

said ceramic element has a rectangular shape, a plurality of said electrode terminal portions being provided on one outer surface of a pair of outer surfaces opposite to each other, a plurality of said electrode terminal portions being provided on the other surface of the pair of outer surfaces;

said conductive wire member is positioned to attach to each of said electrode terminal portions of both outer surfaces;

at least one said insulation member is disposed on an outside of said conductive wire members; and said ring member has two inner surfaces opposite to each other, and compressedly sandwiches said ceramic element, said electrode terminal portions, said conductive wire member, and said insulation member.

17. A ceramic application electronic device according to claim 13, wherein a pair of electrodes of said plurality of electrode terminal portions of said ceramic element is formed for a heater circuit which generates an effective temperature condition to detect the concentration of the specific component of the exhaust gas; and remaining electrodes are formed to pick up and/or apply a voltage effective for detecting a specific component of the exhaust gas.

18. A ceramic application electronic device according to claim 17, wherein said electrode terminal portions, said conductive wire members and said insulation members are disposed on the outer surfaces of said ceramic element to be symmetrical with respect to a center face of said ceramic element, which are compressedly sandwiched by a rectangular ring member by shrink-fitting.

19. A ceramic application electronic device according to claim 1, wherein said ceramic application device is a ceramic heater for a vehicle, and said electrode terminal portion is connected to a heater circuit formed in said ceramic element.

20. A ceramic application electronic device according to claim 1, wherein said ceramic application device is a ceramic glow plug for a vehicle, and a heater circuit embedded in at least top end portion of said ceramic element for heating a mixed gas in a combustion chamber so that the mixed gas is ignited.

21. A method for manufacturing a ceramic application electronic device comprising the steps of:

attaching a conductive wire member to an electrode terminal portion which is formed to expose an outside of a ceramic element;

disposing an electric insulation member at an outside of said conductive wire member to position and fix said conductive wire member, said electrode terminal portion, and said electric insulation member; and clamping a metallic ring member to an outside of said electrode terminal portion, said conductive member, and said insulation member by shrink-fitting so that the conductive wire member is press-fitted to said electrode terminal portion and said insulation member is sandwiched between said ring member and said conductive wire portion.

22. A method for manufacturing a ceramic application electronic device according to claim 21, wherein said ceramic element has a rectangular cross section and has said electrode terminal portions symmetrically provided on opposite outer surfaces of said ceramic element, wherein said conductive wire member and said insulation member are symmetrically arranged and positioned on the outer surface of said ceramic element and said electrode terminal portions with respect to said ceramic element; and further wherein while maintaining the symmetrical condition, said metallic ring member having said rectangular shape is clamped to the outside of said electrode terminal portion, said conductive material, and said insulation member by shrink-fitting to press-fit said conductive material to said electrode terminal portion as well as said insulation member is sandwiched between said ring member and said conductive wire portion.

23. A method for manufacturing a ceramic application electronic device according to claim 21, wherein the shrink-fitting clamping of said ring member is performed by press-fitting; a taper inner face spreading toward an outer side is formed on an inner surface of an opening portion in an entrance side of the press-fitting; a slant outer surface corresponding to the tapered inner surface is formed on an outer surface of an end portion in a side of said insulation member where the press-fitting is subjected; and the tapered inner surface of said ring member compressedly attaches to the slant outer surface of said insulation member to generate relative slipping so as to progress the press-fitting of said ring member.

* * * * *

UNITED STATES PATENT AND TRADEMARK OFFICE
CERTIFICATE OF CORRECTION

PATENT NO. : 6,082,175
DATED : July 4, 2000
INVENTOR(S) : Yoshikawa et al.

It is certified that error appears in the above-identified patent and that said Letters Patent is hereby corrected as shown below:

Item [57] Abstract:

Line 7, change "component" to --components--.

Line 11, change "expose" to --exposure--.

Line 22, change "temperature" to --temperatures--.

Signed and Sealed this

Seventeenth Day of April, 2001

*Attest:*

NICHOLAS P. GODICI

*Attesting Officer*        *Acting Director of the United States Patent and Trademark Office*